US011814628B2

(12) United States Patent
Van Oosterwijk et al.

(10) Patent No.: US 11,814,628 B2
(45) Date of Patent: Nov. 14, 2023

(54) COMPOSITION AND METHOD OF AN ORALLY ADMINISTERED ANTIMICROBIAL PEPTIDE VECTORED IN A BACTERIAL EXPRESSION VEHICLE

(71) Applicants: US Biologic, Inc., Memphis, TN (US); The United States of America as represented by the Secretary of Agriculture, Washington, DC (US)

(72) Inventors: Jolieke Gerdy Van Oosterwijk, Memphis, TN (US); Luciana Meirelles Richer, Memphis, TN (US); Douglas Steven Zatechka, Cordova, TN (US); Woohyun Kim, Ellicott city, MD (US); Hyun Soon Lillehoj, West Friendship, MD (US); Cyril Gray, Bethesda, MD (US); Christopher Anthony Przybyszewski, Southhaven, MS (US)

(73) Assignee: US Biologic, Inc, Memphis, TN (US)

( * ) Notice: Subject to any disclaimer, the term of this patent is extended or adjusted under 35 U.S.C. 154(b) by 0 days.

(21) Appl. No.: 18/008,512

(22) PCT Filed: Jun. 14, 2021

(86) PCT No.: PCT/US2021/037190
§ 371 (c)(1),
(2) Date: Dec. 6, 2022

(87) PCT Pub. No.: WO2021/257434
PCT Pub. Date: Dec. 23, 2021

(65) Prior Publication Data

US 2023/0272407 A1 Aug. 31, 2023

Related U.S. Application Data

(60) Provisional application No. 63/188,894, filed on May 14, 2021, provisional application No. 63/040,718, filed on Jun. 18, 2020.

(51) Int. Cl.

| | |
|---|---|
| ***C12N 15/75*** | (2006.01) |
| ***A61K 9/00*** | (2006.01) |
| ***A61K 35/742*** | (2015.01) |
| ***C07K 14/465*** | (2006.01) |

(52) U.S. Cl.
CPC ............ *C12N 15/75* (2013.01); *A61K 9/0053* (2013.01); *A61K 35/742* (2013.01); *C07K 14/465* (2013.01)

(58) Field of Classification Search
CPC .... C12N 15/75; A61K 9/0053; A61K 35/742; C07K 14/465
See application file for complete search history.

(56) References Cited

U.S. PATENT DOCUMENTS

| | | | |
|---|---|---|---|
| 11,291,695 B2 * | 4/2022 | Sandvang | C12N 1/205 |
| 2012/0245082 A1 | 9/2012 | Lillehoj et al. | |
| 2021/0283198 A1 * | 9/2021 | Yu | A23K 20/195 |

FOREIGN PATENT DOCUMENTS

| | | |
|---|---|---|
| CN | 106434728 | 8/2020 |

OTHER PUBLICATIONS

Gary Benzion, International Preliminary Report on Patentability PCT/US21/037190, IPEA, dated Jun. 7, 2021, 1-11, PCT.
Kari Rodriquez, International Search Report and Written Opinion PCT/US21/037190, ISA, dated Dec. 9, 2021, 1-12, PCT.
Volzing et. al,. Antimicrobial peptides targeting Gram-negative pathogens, produced and delivered by lactic acid bacteria. ACS Synth Biol. Nov. 15, 2013;2(11):643-50. doi: 10.1021/sb4000367. Epub Jul. 10, 2013.

* cited by examiner

*Primary Examiner* — David C Thomas
(74) *Attorney, Agent, or Firm* — Veritay Group IP PLLC; Susan B. Fentress

(57) ABSTRACT

The inventive subject matter includes an antimicrobial peptide vectored composition made of a bacterial protein expression vehicle expressing one or more recombinant antimicrobial peptide effector molecules. More specifically these novel recombinant antimicrobial peptide effector molecules exhibit preferential anti-microbial activity. The utility of the current inventive subject matter has demonstrated a reduced viability of Eimeira acervulina sporozoites in vitro using a sporozoite killing assay. More specifically, the antimicrobial peptide vectored composition is a bacterial protein expression vehicle expressing one or more recombinant antimicrobial peptide effector molecules, wherein the one or more recombinant antimicrobial peptide effector molecules are engineered from a NK-lysin gene and the one or more recombinant antimicrobial peptide effector molecules are engineered to express functionally active NK-2.

2 Claims, 16 Drawing Sheets

Specification includes a Sequence Listing.

SEQ ID_NK2 Insert Sequence:

*GAGCTC*ATGGCTGCTGCTCTTATCGTTCTTCTTGCTCT
TGGCGCTGCTGTTCAAGTTGCTGTTACACGTCGTCAA
CGTTCTATCTGCAAACAACTTCTTAAAAAACTTCGTC
AACAACTTTCTGATGCTCTTCAAAACAACGATGATCC
TGGCGGCGGCGCTGCTGCTCTTATCGTTCTTCTTGCT
CTTGGCGCTGCTGTTCAAGTTGCTGTTACACGTCGTC
AACGTTCTATCTGCAAACAACTTCTTAAAAAACTTCG
TCAACAACTTTCTGATGCTCTTCAAAACAACGATGAT
CCTGGCGGCGGCGCTGCTGCTCTTATCGTTCTTCTTG
CTCTTGGCGCTGCTGTTCAAGTTGCTGTTACACGTCG
TCAACGTTCTATCTGCAAACAACTTCTTAAAAAACTT
CGTCAACAACTTTCTGATGCTCTTCAAAACAACGATC
CTTAA*CTCGAG*

*SEQ ID NO: 1*

FIG. 7A

SEQ IDs (5' to 3'):

SEQ ID_NK2 Insert Primer
F: GCTAGTAACATCTGACCGAGATTTTTTTGAGCAACTGGATCC
*SEQ ID NO: 2*

SEQ ID_NK2 Insert Primer R: CAACTGCAGCGGCTAGCCCCTC
*SEQ ID NO: 3*

SEQ ID_NK2 Insert Primer F: GCACAGAAAAACCCCATCT
*SEQ ID NO: 4*

SEQ ID_NK2 Insert Primer R: AAGAATATTTGGAGAGCACCG
*SEQ ID NO: 5*

FIG. 7B

Body weights of *Eimeria acervulina* -infected chickens following treatment with *Bacillus subtilis* expressing cNK-2

| | CON | NC | EV6 | EV8 | EV10 | NK6 | NK8 | NK10 | SEM | *P*-value | | |
|---|---|---|---|---|---|---|---|---|---|---|---|---|
| | | | | | | | | | | Treatment | Linearity (dose response) | |
| | | | | | | | | | | | EV | NK |
| Body weight, g | | | | | | | | | | | | |
| D 14 | 397 | 394 | 398 | 399 | 390 | 393 | 392 | 391 | 14.1 | 1.000 | 0.661 | 0.998 |
| D 17 (2 dpi) | 579 | 547 | 566 | 570 | 591 | 569 | 565 | 575 | 15.4 | 0.689 | 0.352 | 0.328 |
| D 21 (6 dpi) | 854[a] | 751[c] | 753[c] | 750[c] | 749[c] | 742[c] | 760[c] | 791[c] | 20.9 | 0.006 | 0.934 | **0.030** |
| D 24 (9 dpi) | 1,060[a] | 940[c] | 944[c] | 957[bc] | 957[bc] | 967[bc] | 962[bc] | 1,009[ab] | 25.3 | 0.022 | 0.764 | **0.025** |
| D 28 (13 dpi) | 1,384[a] | 1,251[b] | 1,256[b] | 1,263[b] | 1,258[b] | 1,257[b] | 1,269[b] | 1,301[ab] | 32.3 | 0.079 | 0.996 | 0.154 |
| Average daily gain, g | | | | | | | | | | | | |
| D 14 to 17 (-1 to 2 dpi) | 56.1 | 55.9 | 56.1 | 57.1 | 56.9 | 55.1 | 55.2 | 54.9 | 1.9 | 0.986 | 0.814 | 0.786 |
| D 17 to 21 (2 to 6 dpi) | 68.7[a] | 51.1[bc] | 46.8[cde] | 45.2[cde] | 39.9[e] | 43.2[cde] | 48.9[bc] | 54.0[b] | 3.5 | 0.001 | **0.013** | **0.011** |
| D 21 to 24 (6 to 9 dpi) | 68.8[bc] | 62.5[d] | 63.9[cd] | 68.9[bc] | 66.0[cd] | 75.1[a] | 67.1[bcd] | 72.8[ab] | 2.2 | 0.001 | 0.654 | **0.008** |
| D 24 to 28 (9 to 13 dpi) | 81.2 | 77.8 | 77.9 | 76.7 | 73.1 | 72.6 | 77.0 | 73.2 | 2.1 | 0.064 | 0.104 | 0.136 |
| D 17 to 24 (2 to 9 dpi) | 68.7[a] | 56.0[c] | 54.1[cd] | 55.3[cd] | 51.0[d] | 57.0[bc] | 56.8[bcd] | 62.1[b] | 2.0 | 0.001 | 0.125 | **0.007** |
| D 17 to 28 (2 to 13 dpi) | 61.9[a] | 54.1[bc] | 53.1[bc] | 53.3[bc] | 50.0[c] | 52.8[bc] | 54.1[bc] | 56.0[b] | 1.6 | 0.001 | 0.107 | 0.121 |

D = day, dpi = days post-infection, SEM = standard error of the mean. All chickens except CON were infected by oral gavage at day 15 with 5,000 oocysts/chicken of *E. acervulina*. *Bacillus subtilis* were administrated by oral gavage daily from 14 to 16 d. EV= *Bacillus subtilis* carrying empty vector, NK= *Bacillus subtilis* expressing cNK-2 NC = No *Bacillus subtilis*, EV6 = *Bacillus subtilis* (empty vector) at $10^6$ cfu/day, EV8 = *Bacillus subtilis* (empty vector) at $10^8$ cfu/day, EV10 = *Bacillus subtilis* (empty vector) at $10^6$ cfu/day, NK6 = *Bacillus subtilis* expressing cNK-2 at $10^6$ cfu/day, NK8 = *Bacillus subtilis* expressing cNK-2 at $10^8$ cfu/day, NK10 = *Bacillus subtilis* expressing cNK-2 at $10^{10}$ cfu/day, a~eMeans in the same row with different superscripts differ ($P < 0.05$) and the difference was revaluated by PDIFF option in SAS when P-value between treatments was less than 0.05.

FIG. 14

SEQUENCE LISTING

```
<160> NUMBER OF SEQ ID NOS: 28

<210> SEQ ID NO 1
<211> LENGTH: 456
<212> TYPE: DNA
<213> ORGANISM: Artificial Sequence
<220> FEATURE:
<223> OTHER INFORMATION: synthetic Gallus gallus
<220> FEATURE:
<221> NAME/KEY: misc_binding
<222> LOCATION: (1)..(6)
<223> OTHER INFORMATION: Xho1 restriction sites
<220> FEATURE:
<221> NAME/KEY: misc_signal
<222> LOCATION: (7)..(80)
<223> OTHER INFORMATION: signal sequence
<220> FEATURE:
<221> NAME/KEY: CDS
<222> LOCATION: (81)..(149)
<223> OTHER INFORMATION: mRNA coding sequence
<220> FEATURE:
<221> NAME/KEY: misc_signal
<222> LOCATION: (150)..(230)
<223> OTHER INFORMATION: signal sequence
<220> FEATURE:
<221> NAME/KEY: CDS
<222> LOCATION: (231)..(299)
<223> OTHER INFORMATION: mRNA coding sequence
<220> FEATURE:
<221> NAME/KEY: misc_signal
<222> LOCATION: (300)..(380)
<223> OTHER INFORMATION: signal sequence
<220> FEATURE:
<221> NAME/KEY: misc_signal
<222> LOCATION: (381)..(446)
<223> OTHER INFORMATION: signal sequence
<220> FEATURE:
<221> NAME/KEY: misc_feature
<222> LOCATION: (447)..(450)
<223> OTHER INFORMATION: Arginine bridge Sequence
<220> FEATURE:
<221> NAME/KEY: misc_binding
<222> LOCATION: (451)..(456)
<223> OTHER INFORMATION: Xho1 restriction sites

<400> SEQUENCE: 1

gagctcatgg ctgctgctct tatcgttctt cttgctcttg gcgctgctgt tcaagttgct      60

gttacacgtc gtcaacgttc tat ctg caa aca act tct taa aaa act tcg tca     113
                      Tyr Leu Gln Thr Thr Ser     Lys Thr Ser Ser
                      1               5                       10

aca act ttc tga tgc tct tca aaa caa cga tga tcc tggcggcggc           159
Thr Thr Phe     Cys Ser Ser Lys Gln Arg     Ser
                    15                      20

gctgctgctc ttatcgttct tcttgctctt ggcgctgctg ttcaagttgc tgttacacgt    219

cgtcaacgtt c tat ctg caa aca act tct taa aaa act tcg tca aca act     269
             Tyr Leu Gln Thr Thr Ser     Lys Thr Ser Ser Thr Thr
                         25                      30
```

```
ttc tga tgc tct tca aaa caa cga tga tcc tggcggcggc gctgctgctc        319
Phe     Cys Ser Ser Lys Gln Arg     Ser
            35                      40

ttatcgttct tcttgctctt ggcgctgctg ttcaagttgc tgttacacgt cgtcaacgtt    379

ctatctgcaa acaacttctt aaaaaacttc gtcaacaact ttctgatgct cttcaaaaca    439

acgatcctta actcgag                                                   456
```

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct

<400> SEQUENCE: 2

```
Tyr Leu Gln Thr Thr Ser
1               5
```

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct

<400> SEQUENCE: 3

```
Lys Thr Ser Ser Thr Thr Phe
1               5
```

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

```
Cys Ser Ser Lys Gln Arg
1               5
```

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

```
Tyr Leu Gln Thr Thr Ser
1               5
```

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

```
Lys Thr Ser Ser Thr Thr Phe
1               5
```

<210> SEQ ID NO 7
<211> LENGTH: 6

```
<212> TYPE: PRT
<213> ORGANISM: Artificial Sequence
<220> FEATURE:
<223> OTHER INFORMATION: Synthetic Construct

<400> SEQUENCE: 7

Cys Ser Ser Lys Gln Arg
1               5

<210> SEQ ID NO 8
<211> LENGTH: 42
<212> TYPE: DNA
<213> ORGANISM: Artificial Sequence
<220> FEATURE:
<223> OTHER INFORMATION: synthetic Gallus gallus

<400> SEQUENCE: 8

gctagtaaca tctgaccgag atttttttga gcaactggat cc                          42

<210> SEQ ID NO 9
<211> LENGTH: 22
<212> TYPE: DNA
<213> ORGANISM: Artificial Sequence
<220> FEATURE:
<223> OTHER INFORMATION: synthetic Gallus gallus

<400> SEQUENCE: 9

caactgcagc ggctagcccc tc                                                22

<210> SEQ ID NO 10
<211> LENGTH: 19
<212> TYPE: DNA
<213> ORGANISM: Artificial Sequence
<220> FEATURE:
<223> OTHER INFORMATION: synthetic Gallus gallus

<400> SEQUENCE: 10

gcacagaaaa accccatct                                                    19

<210> SEQ ID NO 11
<211> LENGTH: 21
<212> TYPE: DNA
<213> ORGANISM: Artificial Sequence
<220> FEATURE:
<223> OTHER INFORMATION: synthetic Gallus gallus

<400> SEQUENCE: 11

aagaatattt ggagagcacc g                                                 21

<210> SEQ ID NO 12
<211> LENGTH: 27
<212> TYPE: PRT
<213> ORGANISM: Gallus gallus

<400> SEQUENCE: 12

Arg Arg Gln Arg Ser Ile Cys Lys Gln Leu Leu Lys Lys Leu Arg Gln
1               5                   10                  15

Gln Leu Ser Asp Ala Leu Gln Asn Asn Asp Asp
            20                  25

<210> SEQ ID NO 13
<211> LENGTH: 20
<212> TYPE: DNA
<213> ORGANISM: Unknown
<220> FEATURE:
<223> OTHER INFORMATION: Forward primer for target gene GAPDH
```

-continued

<400> SEQUENCE: 13
ggtggtgcta agcgtgttat 20

<210> SEQ ID NO 14
<211> LENGTH: 20
<212> TYPE: DNA
<213> ORGANISM: Unknown
<220> FEATURE:
<223> OTHER INFORMATION: Reverse primer for target gene GAPDH

<400> SEQUENCE: 14
acctctgtca tctctccaca 20

<210> SEQ ID NO 15
<211> LENGTH: 21
<212> TYPE: DNA
<213> ORGANISM: Unknown
<220> FEATURE:
<223> OTHER INFORMATION: Forward primer for target gene JAM-2

<400> SEQUENCE: 15
agcctcaaat gggattggat t 21

<210> SEQ ID NO 16
<211> LENGTH: 21
<212> TYPE: DNA
<213> ORGANISM: Unknown
<220> FEATURE:
<223> OTHER INFORMATION: Reverse primer for target gene JAM-2

<400> SEQUENCE: 16
catcaacttg cattcgcttc a 21

<210> SEQ ID NO 17
<211> LENGTH: 21
<212> TYPE: DNA
<213> ORGANISM: Unknown
<220> FEATURE:
<223> OTHER INFORMATION: Forward primer for target gene OCLN

<400> SEQUENCE: 17
gagcccagac taccaaagca a 21

<210> SEQ ID NO 18
<211> LENGTH: 23
<212> TYPE: DNA
<213> ORGANISM: Unknown
<220> FEATURE:
<223> OTHER INFORMATION: Reverse primer for target gene OCLN

<400> SEQUENCE: 18
gcttgatgtg gaagagcttg ttg 23

<210> SEQ ID NO 19
<211> LENGTH: 19
<212> TYPE: DNA
<213> ORGANISM: Unknown
<220> FEATURE:
<223> OTHER INFORMATION: Forward primer for target gene ZO-1

<400> SEQUENCE: 19
ccgcagtcgt tcacgatct 19

<210> SEQ ID NO 20

-continued

<211> LENGTH: 23
<212> TYPE: DNA
<213> ORGANISM: Unknown
<220> FEATURE:
<223> OTHER INFORMATION: Reverse primer for ZO-1

<400> SEQUENCE: 20
ggagaatgtc tggaatggtc tga 23

<210> SEQ ID NO 21
<211> LENGTH: 19
<212> TYPE: DNA
<213> ORGANISM: Unknown
<220> FEATURE:
<223> OTHER INFORMATION: Forward primer for target gene MUC-2

<400> SEQUENCE: 21
gcctgcccag gaaatcaag 19

<210> SEQ ID NO 22
<211> LENGTH: 20
<212> TYPE: DNA
<213> ORGANISM: Unknown
<220> FEATURE:
<223> OTHER INFORMATION: Reverse primer for target gene MUC-2

<400> SEQUENCE: 22
cgacaagttt gctggcacat 20

<210> SEQ ID NO 23
<211> LENGTH: 21
<212> TYPE: DNA
<213> ORGANISM: Unknown
<220> FEATURE:
<223> OTHER INFORMATION: Forward primer for target gene HMOX-1

<400> SEQUENCE: 23
ctggagaagg gttggctttc t 21

<210> SEQ ID NO 24
<211> LENGTH: 21
<212> TYPE: DNA
<213> ORGANISM: Unknown
<220> FEATURE:
<223> OTHER INFORMATION: Reverse primer for target gene HMOX-1

<400> SEQUENCE: 24
gaagctctgc ctttggctgt a 21

<210> SEQ ID NO 25
<211> LENGTH: 20
<212> TYPE: DNA
<213> ORGANISM: Unknown
<220> FEATURE:
<223> OTHER INFORMATION: Forward primer for target gene SOD1

<400> SEQUENCE: 25
attaccggct tgtctgatgg 20

<210> SEQ ID NO 26
<211> LENGTH: 20
<212> TYPE: DNA
<213> ORGANISM: Unknown
<220> FEATURE:
<223> OTHER INFORMATION: Reverse primer for target gene SOD1

<400> SEQUENCE: 26

-continued

```
cctccctttg cagtcacatt                                               20


<210> SEQ ID NO 27
<211> LENGTH: 20
<212> TYPE: DNA
<213> ORGANISM: Unknown
<220> FEATURE:
<223> OTHER INFORMATION: Forward primer for target gene CAT

<400> SEQUENCE: 27

actgcaaggc gaaagtgttt                                               20


<210> SEQ ID NO 28
<211> LENGTH: 20
<212> TYPE: DNA
<213> ORGANISM: Unknown
<220> FEATURE:
<223> OTHER INFORMATION: Reverse primer for target gene CAT

<400> SEQUENCE: 28

ggctatggat gaaggatgga                                               20
```

COMPOSITION AND METHOD OF AN ORALLY ADMINISTERED ANTIMICROBIAL PEPTIDE VECTORED IN A BACTERIAL EXPRESSION VEHICLE

BACKGROUND OF THE INVENTION

Incorporation by reference of the material in the ASCII text file:

Applicant hereby specifically incorporates by reference the files PATENTIN_ST25, created on Mar. 27, 2023 and of 8.65 KB.

Field of Invention

The subject matter disclosed herein provides a recombinant anti-microbial protein expressed from *Bacillus subtilis* strains, which are vectored with the chicken NK lysin gene or cNK-2 peptide gene which can be formulated as an orally delivered antimicrobial agent.

Background

Avian coccidiosis is caused by several distinct protozoan parasites of the genus *Eimeria* and is characterized by high mortality and poor performance with reduced feed intake with estimated annual economic loss of more than $3.2 million, Restrictions on the use of antimicrobials in food production enacted by health officials and those arising from consumer choices to purchase meat produced without antibiotics has limited the tools veterinarians have today. Overuse of antibiotics (particularly in the poultry industry) can lead to antimicrobial resistance and has resulted in tremendous market and regulatory agency pressures for alternatives to antibiotics. A need exists for an orally delivered treatment for coccidiosis and other related conditions.

SUMMARY OF THE INVENTION

The inventive subject matter includes an antimicrobial peptide vectored composition made of a bacterial protein expression vehicle expressing one or more recombinant antimicrobial peptide effector molecules. More specifically these novel recombinant antimicrobial peptide effector molecules exhibit preferential anti-microbial activity. In some embodiments, the anti-microbial activity is facilitated via interaction with the lipid bilayer of the parasitic cell form, leading to membrane pore formation and resulting in cell lysis. The utility of the current inventive subject matter has demonstrated a reduced viability of *Eimeira acervulina* sporozoites was shown in vitro using a sporozoite killing assay. More specifically, the antimicrobial peptide vectored composition is a bacterial protein expression vehicle expressing one or more recombinant antimicrobial peptide effector molecules, wherein the one or more recombinant antimicrobial peptide effector molecules are engineered from a NK-lysin gene and the one or more recombinant antimicrobial peptide effector molecules are engineered to express functionally active NK-2. More specifically, the one or more recombinant antimicrobial peptide effector molecules induce cytotoxicity against infectious agents of the phylum of Apicomplexa.

Another novel aspect of this invention includes a process for producing one or more recombinant antimicrobial peptide effector molecules expressed in the context of a bacterial expression vehicle. This process includes the steps of producing the bacterial expression vehicle by culturing a competent bacterium transformed with a replicable plasmid DNA expression construct for the expression of said antimicrobial peptide effector molecules within the context of the competent bacterium and expressing the one or more recombinant antimicrobial peptide effector molecules in said bacterial expression vehicle. More specifically, the bacterial expression vehicle is cultured under a xylose-dependent system for selectable expression and without the use of recombinant antibiotic selectable markers. In one exemplary embodiment the replicable plasmid DNA expression construct consists essentially of SEQ ID NO: 1. In one exemplary embodiment, the one or more recombinant antimicrobial peptide effector molecules are actively secreted into the surrounding liquid carrier matrix, and the actively secreted recombinant antimicrobial peptide effector molecules exhibit cytotoxicity upon microbial cultures.

Another novel aspect of this invention includes a method to treat a subject in need of treatment from for example from an infectious agent. The steps of this method include administering a therapeutically effective amount of the antimicrobial peptide vectored composition made of a bacterial protein expression vehicle expressing one or more recombinant antimicrobial peptide effector molecules, wherein the one or more recombinant antimicrobial peptide effector molecules are engineered from a NK-lysin gene and express functionally active NK-2

In particular, this method is effective wherein the subject is poultry, and the poultry need treatment for Avian coccidiosis, the method including the step of orally administering to the subject a therapeutically effective amount of a stable strain of a probiotic *B. subtilis* to treat an Avian coccidiosis infection.

In particular, this method is useful wherein the subject is poultry, and the poultry are in need of treatment to increase body weight. The inventive subject matter includes the step of orally administering to the subject a therapeutically amount of a stable strain of a probiotic *B. subtilis* expressing cNK-2 to increase body weight of the subject.

Additionally, the inventive subject matter includes treating poultry in of treatment to restore gut microbiome. The method including the step of orally administering to the subject a therapeutically amount of a stable strain of a probiotic *B. subtilis* expressing cNK-2 to restore gut microbiome of the subject.

Another novel aspect of this invention includes preservation of the gut microbiome in *Eimeria* challenged chickens by providing an effective amount of a probiotic expressing cNK-2.

BRIEF DESCRIPTION OF THE DRAWINGS

The novel features of the invention are set forth with particularity in the claims. Features and advantages of the present invention are referred to in the following detailed description, and the accompanying drawings of which:

FIG. 7A shows the SEQ ID_NK2 Insert Sequence.

FIG. 7B shows the primer sequences.

FIG. 14 shows body weight of chicken following treatment. D=day, dpi=days post-infection, SEM=standard error of the mean. All chickens except CON were infected by oral gavage at day 15 with 5,000 oocysts/chicken of *E. acervulina. Bacillus subtilis* were administrated by oral gavage daily from 14 to 16 d. EV=*Bacillus subtilis* carrying empty vector, NK=*Bacillus subtilis* expressing cNK-2 NC=No *Bacillus subtilis,* EV6=*Bacillus subtilis* (empty vector) at $10^6$ cfu/day, EV8=*Bacillus subtilis* (empty vector) at $10^8$ cfu/day, EV10=*Bacillus subtilis* (empty vector) at $10^6$ cfu/day, NK6=*Bacillus subtilis* expressing cNK-2 at $10^6$ cfu/day, NK8=*Bacillus subtilis* expressing cNK-2 at $10^8$ cfu/day, NK10=*Bacillus subtilis* expressing cNK-2 at $10^{10}$ cfu/day, $^{a\sim e}$ Means in the same row with different superscripts differ (P<0.05) and the difference was revaluated by PDIFF option in SAS when P-value between treatments was less than 0.05.

DETAILED DESCRIPTION OF THE INVENTION

Figure 1:
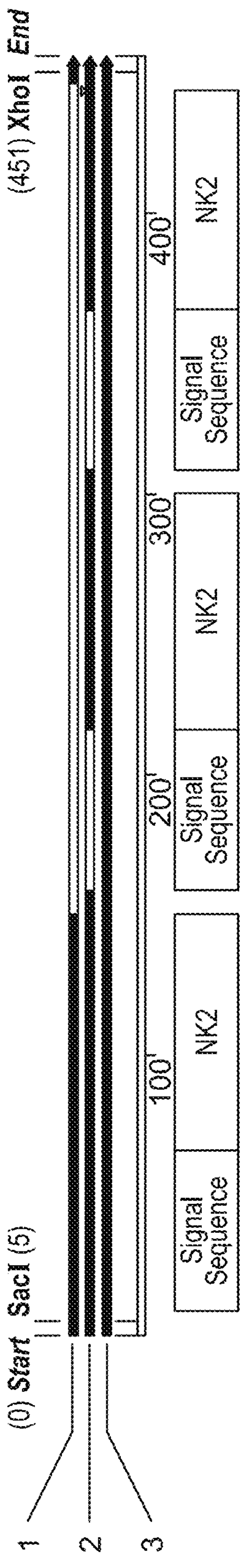
FIG. 1 provides a linear map representing the molecular orientation of the engineered NK2 constructs. The sequence was codon-optimized for expression in *Bacillus subtilis.* Contig 1 was engineered to express a single secretory signal sequence cloned in 5' to the NK2 expression sequence. Contig 2 was engineered to express a single secretory signal sequence cloned in 5' to a triple NK2 sequence repeat. Contig 3 was engineered to express a triple secretory signal sequence clone in 5' to a single NK2 expression sequence. The sequences for the NK2 constructs were flanked with SacI and XhoI to facilitate cloning.

*Bacillus subtilis,* which is vectored to carry chicken NK lysin gene or cNK-2 peptide gene to express recombinant anti-microbial proteins is provided. Two clones of recombinant *Bacillus subtilis* were selected based on their ability to secrete cNK-2 peptide that have bioactivity against live sporozoite stage of *Eimeria* parasites. The accompanying figures show that the codon-optimized chicken NK-2 sequence was cloned into a high copy expression vector under the control of the xylose-inducible selectable promotor. The expression of chicken NK-2 protein from *Bacillus subtilis* and the antimicrobial effect against *Eimeira acervulina* sporozoites were evaluated in vitro using a sporozoite killing assay. A stable strain is a strain that has a plasmid incorporated so that all daughter cells get at least one plasmid during cell division, and no loss of recombinant protein expression is observed throughout multiple passages and generations.

The details of one or more embodiments of the presently disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as commonly understood by one of ordinary skill in the art to which the presently disclosed subject matter belongs. Although any methods, devices, and materials similar or equivalent to those described herein can be used in the practice or testing of the presently disclosed subject matter, representative methods, devices, and materials are now described. Following long-standing patent law convention, the terms "a", "an", and "the" refer to "one or more" when used in this application, including the claims. Thus, for example, reference to "a cell" includes a plurality of such cells, and so forth. All references to singular characteristics or limitations of the present disclosure shall include the corresponding plural characteristic(s) or limitation(s) and vice versa, unless otherwise specified or clearly implied to the contrary by the context in which the reference is made. All combinations of method or process steps as used herein can be performed in any order, unless otherwise specified or clearly implied to the contrary by the context in which the referenced combination is made. The methods and compositions of the present disclosure, including components thereof, can comprise, consist of, or consist essentially of the essential elements and limitations of the embodiments described herein, as well as any additional or optional components or limitations described herein or otherwise useful. Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed.

The presently disclosed subject matter relates to a composition and method of using the composition for oral delivery of a biologically active agent to a subject. More particularly, the presently disclosed subject matter relates to a composition made of a substrate and an effective amount of at least one biologically active agent stabilized by layered encapsulation over the substrate and a method of reducing infectious disease by administering the composition to a subject. The presently disclosed subject matter further relates to a method of preparing the composition. In some embodiments of the presently disclosed subject matter, a composition is provided. The composition includes a substrate, an effective amount of an osmotically preconditioned at least one bioactive agent layered over the substrate, and a cross-linking agent. In some embodiments, the at least one bioactive agent is stabilized in a stabilizer under conditions facilitating anhydrobiosis. The term "bioactive agent" refers to an antimicrobial peptide effector molecule.

In some embodiments, the bioactive agent is a recombinant whole-cell bacterium molecular engineered to express one or more protein. As used herein, the "recombinant whole-cell bacteria engineered to express one or more protein" is a bacterial expression vehicle for the expression of a therapeutic protein. As used herein, "whole-cell bacteria" refers to bacterial cells, maintained under conditions that retain the bacterial cellular structural integrity, that is, whole-cell structural integrity. Conditions favorable for the structural integrity of the bioactive agent is defined as stabilized.

In some embodiments, the whole-cell bacteria include, but is not limited to preparations of *B. subtilis.* As used herein, the bioactive agent, or biologically active agent, is a whole-cell bacterial protein expression vehicle. As used herein cultures of *B. subtilis* are used as a collective homogeneous, clonally expanded preparation of the bacterial expression vehicle. As used herein, bacterial expression vehicles are considered biological vehicles, or biologics, wherein the composition is made of components of living biological organisms. The use of bacterial expression vehicles as biologics that present with prophylactic and/or therapeutic intervention strategies in the control of disease has increased recently given the application of recombinant expression technologies. As a biologic, with added commensalism such as *Bacillus subtilis* have emerged in the biotechnology space as promising systems for recombinant protein expression technology given their GRAS (Generally Recognized as Safe) determination by the US Food and Drug Administration (FDA). However, *B. subtilis* strains are only now presenting with the expression systems supporting recombinant protein technologies.

In some embodiments, the bacterial expression system bacteria are molecular engineered to express one or more proteins, which are expressed using a recombinant plasmid expression vector transformation event. As used herein, "molecular engineered" refers to the molecular biological technique of biosynthetic molecular cloning of genes identified for the expression of specific proteins of interest into the plasmid expression vector. As used herein, the plasmid expression vector is then used to transform a competent bacterium into the bacterial expression system. A competent bacterium are bacterial cells treated to accept a plasmid.

In some embodiments, the recombinant bacteria are lyophilized/freeze-dried. In some embodiments, the recombinant bacteria are air-dried as an anhydrobiotic preparation. In still other embodiments, the recombinant bacteria are rendered metabolically inactive via sporulation as an anhydrobiotic preparation. As used in the presently disclosed subject matter, the induction of anhydrobiosis is defined as a biologically stable state of desiccation, and as used herein is therefore a downstream bio-processing step introduced during production as a means to effectively dry the biologic product in a stable state to facilitate and accommodate the subsequent biologistics requirements.

Currently employed strategies for bulk anhydrobiotic processing include lyophilization (freeze-drying) of the biologic product resulting in a physical powder. However, the process of lyophilization can result in a significant loss of potency of whole-cell protein expression vehicles. Further, lyophilization is not easily scalable and can be costly for industrial application; as a powder, the resultant product must be further formulated for stability, application, and administration as an antimicrobial peptide effector molecule.

Additional anhydrobiotic processing strategies have involved the use microencapsulation technologies for entrapping biologics in spheronized microbeads. Such technologies are employed in the processing of probiotic bacteria of the phylogenetic class Bacilli to include the lactic acid bacteria (LAB) and the *Bacillus* species for use in the probiotics industry. Further, the employment of downstream processing that results in the generation of microencapsulated biologics in the form of spherical microbeads, a product that presents as a course powder of beads the size of which may range from 100 μm to several thousand μm, may not be of a size practical for targeted distribution. Such beads are also of a composition of cellulose, specifically microcrystalline cellulose (MCC), a composition that may not be favorable for targeted (attractive) consumption as a bait by reservoir hosts.

Stability measures supporting oral administration of biologics employ the use of enteric protection for effective passage through the gut for specific release at targeted regions of the GI tract. The introduction of enteric stabilization methodologies has been utilized with success in the probiotics industry for administering efficacious doses of probiotic strains as part of a regimen for enhancing the gut microbiome and systemic health. Current strategies employ calcium-alginate encapsulation chemistries, wherein a given concentration of polymeric matrix made of the probiotic in composition with a solution of alginate are dripped via vibrational nozzle, or spray atomized, into a bath of a given concentration of a calcium salt facilitating a cross-linking (microencapsulation) of the polymeric matrix. The resultant microencapsulated probiotic product is retrieved from the calcium bath and subsequently lyophilized yielding the powdered final product for consumption. Powders will need to be applied with uniformity, for quality analysis and dosage standardization, as layers onto baiting substrate options.

Inclusion of the bacterial protein expression vehicle within the context of an oral administration substrate material requires a formulation that extends stability to the bacterial expression vehicle. The bacterial-expression vehicle may be sensitive to heat and pressure, which renders the biologic ineffective if formulated as an amalgam in composition and extruded with the substrate. There is also a need for a unique downstream processing protocol that accommodates the unique biologic nature of the bacterial protein expression vehicle as a means to osmotically precondition the vehicle for anhydrobiosis. As part of this preconditioning protocol, there is a need for establishing the composition and methods for the vehicle preconditioning process, to include the stability carrier matrix formulation and temperature parameters, and the subsequent application of the carrier matrix upon the carrier substrate. Finally, as part of the process for stabilizing the bacterial protein expression vehicle as an antimicrobial peptide effector molecule. for oral administration, there exists a need for enteric stability to specific regions of the gut of the targeted host. In certain embodiments, the composition is a substrate and an effective amount of at least one bioactive agent coated or layered over the substrate. As used herein, the term "substrate" refers to a solid support composition, such as a carrier, onto which may be applied the antimicrobial peptide effector molecules.

In some embodiments, the bioactive agent is osmotically pre-conditioned for anhydrobiosis and stabilization. As used herein, the term "osmotically preconditioned" refers to the use of specific solutes employed to physically stabilize and protect membranes and proteins in intact bacteria prior to drying to desiccation. Non-limiting osmotic preconditioners include plasticizing agents such as sugars, to include sucrose and/or trehalose, or hydroxyectoine. As used herein, the term "anhydrobiosis" refers to the physical state of biological tolerance to desiccation. In some embodiments, the bioactive agent is stabilized in a stabilizer. Stabilization refers to the means of promoting and maintaining the biological activity of the bioactive agent, wherein the whole-cell carrier is structurally maintained for effective presentation of protein as an immunogen. Non-limiting stabilizers incorporate the use of hydrocolloids. As used herein, the term "hydrocolloid" will refer to any material of the colloid family of hydrophilic polymers dispersed in aqueous solution. Hydrocolloids present, in some embodiments, as small particles of about 1 to about 1000 nm in diameter and serve to encapsulate and stabilize biological material. A hydrocolloid of the present disclosure may include, but is not limited to, agar, alginate, carrageenan, chitosan, gelatin, and/or gum. Suitable hydrocolloids may include one or more natural and synthetic polymers, which form colloidal solutions in aqueous systems. Preferable hydrocolloids include polysaccharides, such as alginic acid, sodium alginate, and calcium alginate. Suitable hydrocolloids include polyvinyl pyrrolidones; starch; cellulose and cellulose derivatives, such as ethyl cellulose, methyl cellulose, hydroxypropylmethyl cellulose (HPMC), hydroxypropyl cellulose (HPC), and carboxymethylcellulose (CMC); polyethylene glycol (PEG); or mixtures thereof. As used herein, hydrocolloids are employed as liquid carriers for the at least one bioactive agent for feasible application as a liquid coating around the substrate. In some embodiments, the liquid carrier also serves to include application of visualization tracer formulations. As used herein, visualization tracer formulations include the divalent salts of barium, to include barium sulfate. As used herein, preparation of barium sulfate in the context of the liquid carrier stabilized by layered encapsulation over the substrate provide a means by which substrate administration formulation can be visualized via X-ray for gastro-intestinal (GI) dissolution. As used herein, GI dissolution further provides added assurance of the stabilization of the agent for presentation of the protein payload to the gut-associate lymphoid tissues (GALT). In some embodiments, the liquid carrier also serves to include application of active pharmaceutical ingredients (APIs) as further measure of GALT dissolution and systemic metabolism of the liquid carrier stabilized by layered encapsulation over the substrate. As used herein, APIs can include, but are not limited to, the use of Ivermectin. As used herein, GALT-level dissolution of the API-liquid carrier stabilized by layered encapsulation can be measured via serological assay of Ivermectin by high-pressure liquid chromatography (HPLC),In some embodiments, certain hydrocolloid polymers, such as sodium alginate, may be cross-linked in the presence of a calcium salt. Cross-linking in the presence of a divalent cation such as calcium refers to the capacity to structurally link the polymeric bonds of the hydrocolloid polymer, sodium alginate, to calcium to generate a polymer of calcium alginate cross-linked bonds; calcium ions replace the sodium ions in the alginate polymer yielding what is termed polymerization. Polymerization via cross-linking facilitates the stabilized encapsulation of the antimicrobial peptide effector molecules as used in the presently disclosed subject matter. In some embodiments, the cross-linking agent is a calcium salt. Examples of cross-linking agent include, but are not limited to, calcium lactate, calcium butyrate, calcium chloride, calcium sulfate, calcium carbonate, calcium acetate, or calcium ascorbate. As used in the presently disclosed subject matter, the cross-linking agent facilitates polymerization of the stabilizer. As presented herein the composition of the presently disclosed subject, the composition relates to a composition made of a substrate and an effective amount of at least one biologically active agent stabilized by layered encapsulation over the substrate. As used herein, the term substrate relates to a substance of solid support, suitable for oral consumption, upon which or around which (as a shell or coating) may be applied the osmotically preconditioned stabilized at least one bioactive agent. In some embodiments, the substrate has a mean diameter of from about 100 μm to about 5 cm. In some embodiments, the composition may be of a size of about no more than 10 cm to accommodate consumption by target animal species. In some embodiments of the presently disclosed subject matter, examples of the substrate include, but is not limited to pellet, a chewable, a bead and a powder. In some embodiments, the substrate is a plant-based or earthen-based substance. In some embodiments, the earthen-based substance includes but is not limited to soil or water. In some embodiments, the substrate further includes, but is not limited to, a plant and/or forage material to include grass, herbaceous legumes, tree legumes, silage, or crop residues to include grains such as corn or soybean stover, or other earthen-based substance, such as soil, compost, or addition directly to water. In certain embodiments, the substrate is edible, and appropriate to be fed to animals in a composition. In some embodiments, the substrate can include: a dried pellet or kibble, such as a particle generated by compressing original material, which may be broken up upon mastication into particulate material; and/or a chewable particle, soft and pliable in nature, such that it is not readily broken up or reduced to particulate matter upon mastication but may be readily dissolved; and/or a composition that may bypass the ruminant digestive processes such as a ruminant undegradable protein (RUP) substrate; micro-crystalline cellulose beads or other substrate for employment in the generation and application of antimicrobial peptide effector molecules, in powdered formulation for administration via nasal inhalation, or to be administered directly to water as a hydrocolloidal suspension as an oral administration via drinking; a plant; a food-source, such as a food source that is available in the wild; and/or another earthen substance, soil or other onto which the antimicrobial peptide effector molecule is then dried for stability, or water into which may be applied the antimicrobial peptide effector molecules for consumption by drinking. In some embodiments, the composition further includes a coating on the exterior surface of the composition. In some embodiments, the coating is an enteric coating. In some embodiments, the coating on the exterior surface of the substrate is sequentially applied in layers as a top-dressing and is an enteric coating once cross-linked. In some embodiments, the substrate is in an amount of about 85% to about 99% w/w of the composition. In some embodiments, the stabilizer is in an amount of about 1% to about 15% w/w of the composition. In some embodiments, the effective amount of the bioactive agent is an immunogenically effective amount with the minimal immunizing dosage (MID) of about $5\times10^3$ CFU to about $5\times10^{11}$ CFU. In some embodiments, cross-linking agent is in an amount of about 0.5% to about 7.5% w/w of the composition. Further, in some embodiments, the coating is in an amount of about 1.5% to about 22.5% w/w of the composition.

In some embodiments of the presently disclosed subject matter, a composition for oral delivery of an antimicrobial peptide effector molecules is provided. The composition includes a substrate, an effective amount of at least one antimicrobial peptide effector molecules coated or layered on a substrate, and a cross-linking agent to facilitate the encapsulation of the antimicrobial peptide effector molecules in the stabilizer on the surface of the substrate. In some embodiments, the at least one bioactive agent is stabilized in a stabilizer selected from a group consisting of a hydrocolloid polymer further made of a plasticizing sugar to include sucrose. Still further, in some embodiments, a method of preparing a composition for oral delivery of a bioactive agent is provided. The method includes the steps of uniquely passaging and culturing the at least one bioactive agent; osmotically preconditioning the at least one bioactive agent; stabilizing at least one bioactive agent in a stabilizer; coating the stabilized at least one bioactive agent on to a substrate; applying a cross-linking agent; cross-linking to facilitate gelation or encapsulation of bioactive agent; and drying under forced air at an ambient temperature. In some embodiments, the temperature is in a range of between about −50° C. to about −80° C. In some embodiments, the temperature is in a range of between about 0.03 mBar to about 0.0005 mBar. In some embodiments, the temperature is in a range of between about 20° C. to about 35° C. In some embodiments, a fan drives the ambient temperatures. In some embodiments, the methods further include a step of coating with a confectionary glaze layer on the exterior surface for moisture barrier or flavored attractant. In some embodiments, the method further includes a step of coating with a shellac layer on the exterior surface for moisture barrier.

Current methods for generating calcium-alginate encapsulated biological materials require the generation of hydrogel or calcium-alginate beads. Bead-encapsulated biological materials are generated by the pressurized dispensing of sodium alginate into a volume of calcium salt, a process employing specific encapsulation equipment (an encapsulator) (Mazzitelli et al., *J. Biomat Appl.* 23:123, 2008). Calcium-alginate beads generated by an encapsulator can be harvested and dried for downstream application. The bead format does not render itself beneficial or efficient for the uniform application onto defined substrates for targeted distribution and administration. Ibid.

The presently disclosed subject matter provides a method of preparing a composition for oral delivery of an active bioactive agent. The method includes, for example, the steps of: stabilizing by osmotic conditioning at least one bioactive agent, coating the at least one bioactive agent onto a substrate employing a sodium alginate suspension as a liquid carrier for layered application, cross-linking by a secondary layering of a calcium salt to facilitate layered gelation via calcium-alginate encapsulation of the bacterial protein expression vehicle, and air drying under forced air ambient temperatures yielding a layered anhydrobiotic preparation of the active bioactive agent. In some embodiments, the methods of the present disclosure include a step of coating the bacterial protein expression vehicle and/or the substrate with a glaze layer on the exterior surface to provide a moisture barrier and/or flavored attractant. As such, employment of the more simplified sequential spray coating and layering application of the encapsulated biological materials provides an efficient and commercially viable method for the applying stabilized biologically active materials as layered coatings over a substrate. Encapsulated layering onto substrates provides a carrier method for targeted distribution of the biologically active agent.

As used herein, the term "antimicrobial peptide vectored composition" is defined as the *B. subtilis* vectored for the expression of secreted antimicrobial peptide. As used herein, the "secreted antimicrobial peptide" represents a recombinant chicken NK lysin or the peptide, cNK-2, which can lyse the invasive forms of *Eimeria.* The term "recombinant antimicrobial peptide effector molecules" is defined as those peptides with an effect upon invasive forms of *Eimeria.* For the purpose of this invention, the sequence "identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other is regarded as a position with non-identical residues. The alignment of the two sequences is performed by the Needleman and Wunsch algorithm (Needleman and Wunsch, J Mol Biol, (1970) 48:3, 443-53). A computer-assisted sequence alignment can be conveniently performed using a standard software program such as GAP which is part of the Wisconsin Package Version 10.1 (Genetics Computer Group, Madison, Wis., USA) using the default scoring matrix with a gap creation penalty of 50 and a gap extension penalty of 3.

An isolated nucleic acid is a nucleic acid the structure of which is not identical to that of any naturally occurring nucleic acid. The term therefore covers, for example, (a) a DNA which has the sequence of part of a naturally occurring genomic DNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library. The term recombinant nucleic acids refer to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Where a recombinant nucleic acid is intended for expression, cloning, or replication of a particular sequence, DNA constructs prepared for introduction into a prokaryotic or eukaryotic host will typically include a replication system (i.e. vector) recognized by the host, including the intended DNA fragment encoding a desired polypeptide, and can also include transcription and translational initiation regulatory sequences operably linked to the polypeptide-encoding segment. Expression systems (expression vectors) can include, for example, an origin of replication or autonomously replicating sequence and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient identity to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) *Current Protocols in Molecular Biology,* John Wiley & Sons, NY, N.Y., for further guidance on hybridization conditions.

Additionally, screening, and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Hybridization-based screening of genetically altered strains typically utilizes homologous nucleic acid probes with identity to a target nucleic acid to be detected. The extent of identity between a probe and a target nucleic acid can be varied according to the particular application. Identity can be 50%-100%. In some instances, such identity is greater than 80%, greater than 85%, greater than 90%, or greater than 95%. The degree of identity or identity needed for any intended use of the sequence(s) is readily identified by one of skill in the art. As used herein percent sequence identity of two nucleic acids is determined using the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See http://www.ncbi.nih.gov.

Preferred host cells are members of the genus *Escherichia,* especially *E. coli.* However, any suitable bacterial or fungal host capable of expressing the described proteins can be utilized. Even more preferably, non-pathogenic, and non-toxigenic strains of such host cells are utilized in practicing embodiments of the disclosed inventions. Examples of workable combinations of cell lines and expression vectors are described in Sambrook et al. (1989); Ausubel et al. (Eds.) (1995) *Current Protocols in Molecular Biology,* Greene Publishing and Wiley Interscience, New York; and Metzger et al. (1988) *Nature,* 334: 31-36. Recombinant host cells, in the present context, are those which have been genetically modified to contain an isolated nucleic molecule of the instant invention. The nucleic acid can be introduced by any means known to the art, which is appropriate for the particular type of cell, including without limitation, transformation, lipofection, electroporation or any other methodology known by those skilled in the art.

The following examples are offered to illustrate, but not to limit the invention.

Avian coccidiosis is caused by several distinct protozoan parasites of the genus Eimeria and is characterized by high mortality and poor performance with reduced feed intake with estimated annual economic loss of more than $3.2 million. The inventive subject matter relates to the development of Bacillus subtilis strains which carry chicken NK lysin gene or cNK-2 peptide gene to express recombinant anti-microbial proteins. Two strains of recombinant Bacillus subtilis have been selected based on their ability to secrete chicken NK lysin and cNK-2 protein that have bioactivity against live sporozoite stage of Eimeria parasites. The accompanying figures show that the codon-optimized chicken NK-2 sequence was cloned into a high copy expression vector with xylose-inducible promotor. The expression of chicken NK-2 protein from *Bacillus subtilis* and the antimicrobial effect against *Eimeira acervulina* sporozoites were evaluated in vitro using a sporozoite killing assay.

Example 1. Now referring to FIGS. 1 and 2, the vectored NK-2 gene used for expression in a bacterial vehicle for protein secretion was based on the chicken NK-lysin sequence, using a triple iteration of the secretory signal sequence upstream of the peptide. The sequence was codon-optimized for expression in *Bacillus subtilis.* The sequence used is shown with the SacI restriction site at the 5' end of the contig, and the XhoI restriction site at the 3' end of the contig; signal sequence is presented in dark grey, and NK-2 mRNA coding sequence in light grey.

The NK-2 sequence was cloned into a high copy *Bacillus subtilis* expression vector, which encodes the endogenous *Bacillus* antitoxin EndoB, under the control of a xylose-inducible promotor. The vectored-amp-NK-2 was expanded using *E. coli* cells and purified using plasmid purification. Sequences were confirmed using Sanger sequencing and the vectored-amp-cNK plasmids were digested using EcoRl and ScaI restriction enzymes (Thermo Fisher), to excise the ampicillin resistance cassette. Bands of correct length were gel purified and digestion and gel purification were repeated to ensure complete digestion and removal of all *E. coli* DNA. The purified linearized plasmids were subsequently religated using Rapid DNA Ligation (Thermo Fisher).

Figure 2:
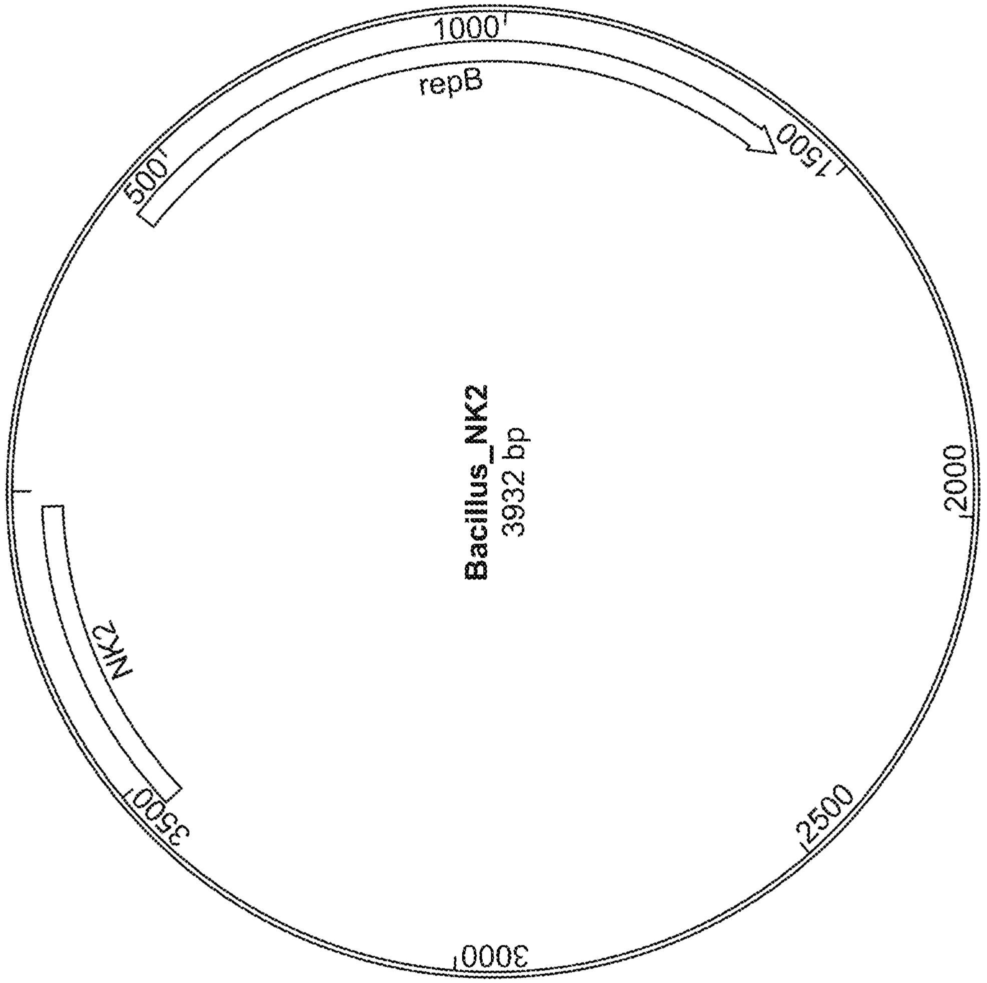
FIG. 2 presents the plasmid vector map of the NK2 construct in the context of the *Bacillus* expression system.
Figure 3:
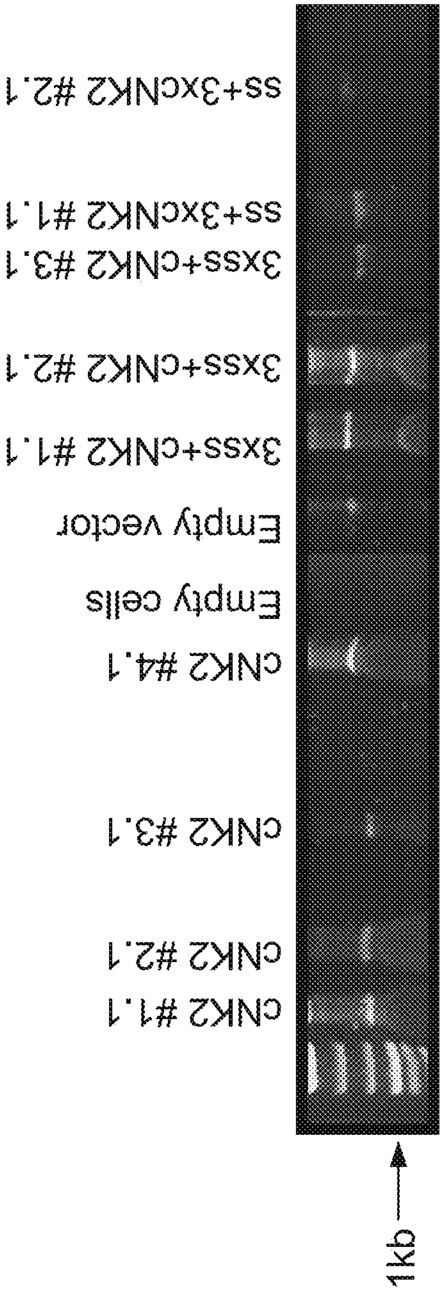
FIG. 3 is a QA analysis using PCR analysis as confirmation of the plasmid insertion of the NK2 contig in various isolated NK2-transformed clones.

Example 1 DATA presented in FIGS. 2 and 3 demonstrate the standard quality analysis conducted for assurance of the unique molecular engineering required to develop the secreted NK2 product. Now referring to FIG. 2, competent *Bacillus subtilis* cells (strain WB800N) were created using culture to stationary growth phase at an $OD_{600}$ of 0.05 in medium containing 0.2% $(NH_4)_2SO_4$, 1.4% $K_2HPO_4$, 0.6% $KH_2PO_4$, 0.0012% $MgSO_4$, 0.1% sodium citrate, 0.5% w/v glucose, 0.02% w/v L-tryptophan, 0.002% w/v casamino acids, 0.5% w/v yeast extract (Difco), 0.8% w/v arginine, and 0.04% histidine (Klein). Competent cells were transformed with the representative *Bacillus*_NK2 expression plasmid using 0.1M EGTA at 1:100 in medium containing 0.2% $(NH_4)_2SO_4$, 1.4% $K_2HPO_4$, 0.6% KH2PO4, 0.0012% $MgSO_4$, 0.1% sodium citrate, 0.5% w/v glucose, 0.002% w/v L-tryptophan, 0.001% w/v casamino acids, 0.5% w/v yeast extract (Difco), 0.02% $MgCl_2$, and 0.00006% $CaCl_2$. Competent cells successfully transformed with pTTB2-cNK (FIG. 2) were grown on agar plates using 1.6% tryptone, 1% yeast extract, 0.5% NaCl, and selected using 2% xylose for 18 hrs at 37 degrees Celsius.

Now referring to FIG. 3, *Bacillus* cells will produce the endotoxin EndoA during growth, which can only be neutralized using the unstable antitoxin EndoB, encoded by the plasmid. As EndoB in under the control of a xylose-inducible promoter, only cells which have stably incorporated and are consistently expressing the vector will survive under xylose conditions (Pellegrini, Park, Simanshu). Single colonies were sequenced and expanded using 3.2% tryptone, 2% yeast extract, 1% NaCl, and 2% xylose in 100 mL for 72 hrs at 37 degrees Celsius at 250 rpm. Cultures were spun down and pelleted at 5000 g for 10-30 mins for cellular DNA processing and isolation, and supernatant was sterile filtered using a 0.2 micrometer syringe filter to remove cellular debris for secreted protein expression. DNA from isolated cell pellets were purified via miniprep and PCR was employed to confirm the insert incorporation. SEQ IDs for the primers are disclosed herein (see Sequence Listing and FIG. 7B) and were used to amplify two parts of the plasmid: one containing the NK2 insert (SEQ ID NO: 1) (FIG. 7A), and one containing the xylose resistance gene following that which is presented in Yang, 2016. The resulting amplicon is an approximately 1.1 kb product.

Figure 4:
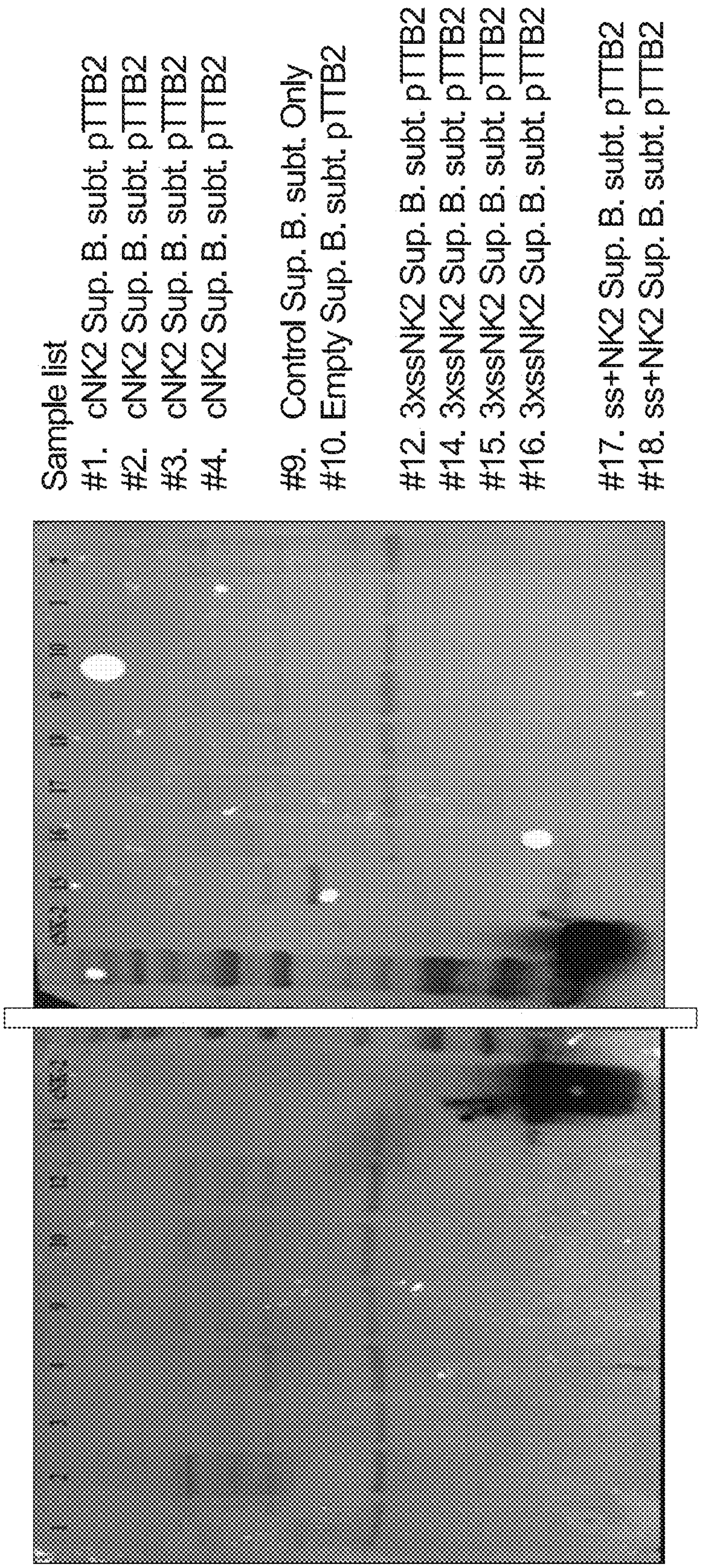
FIG. 4 is a QA analysis using western blot confirmation of the of the expression of the NK2 peptide secreted into the *Bacillus* culture supernatant in various isolated NK2-transformed clones.

Now referring to FIG. 4, clarified culture supernatant from Bacillus cells induced to express and secrete the NK2 product, was subjected to western blot analysis to screen for the secretion of the NK2 product into the surrounding medium. Clone #15 demonstrated positive expression of secreted NK2 into the medium.

Figure 5:
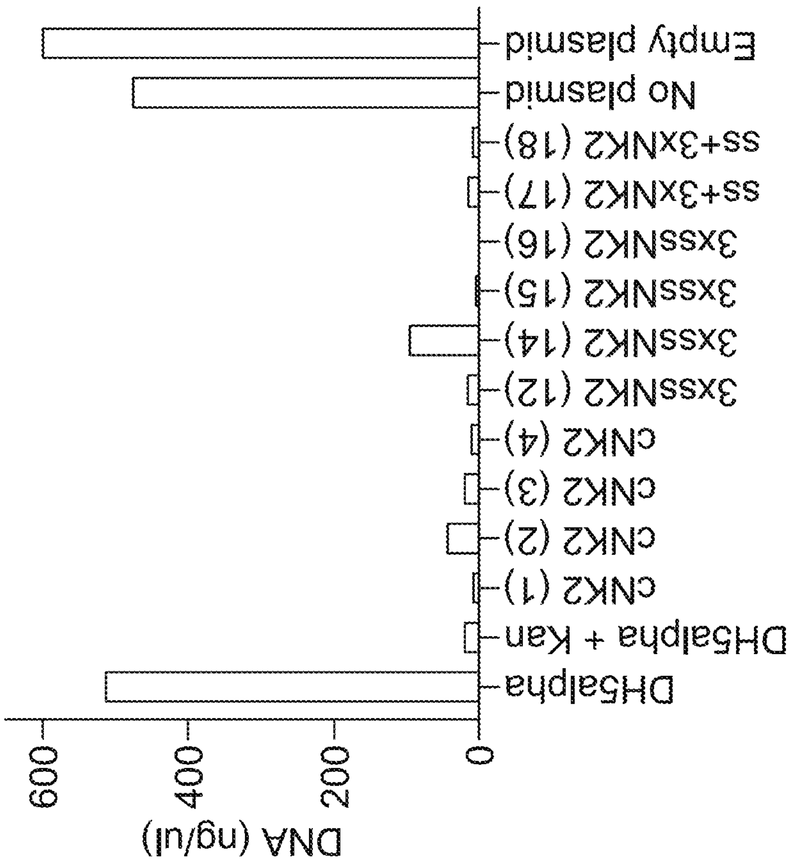
FIG. 5 represents an Efficacy assay on culture supernatant from various isolated clones expressing secreted NK2 peptide. Total DNA was measured after 24 hr growth with or without the presence of cNK2 supernatant from *B. subtillis.* Kanamycin was used as a negative control and DH5alpha cells without any supernatant as a positive control. DH5alpha cells grown in the presence of *B. subtillis* supernatant without NK2 peptide showed no growth inhibition, whereas cells grown in the presence of *B. subtillis* supernatant with NK2 peptide showed growth inhibition comparable to Kanamycin. Clone #15 showed a high killing activity.
Figure 6:
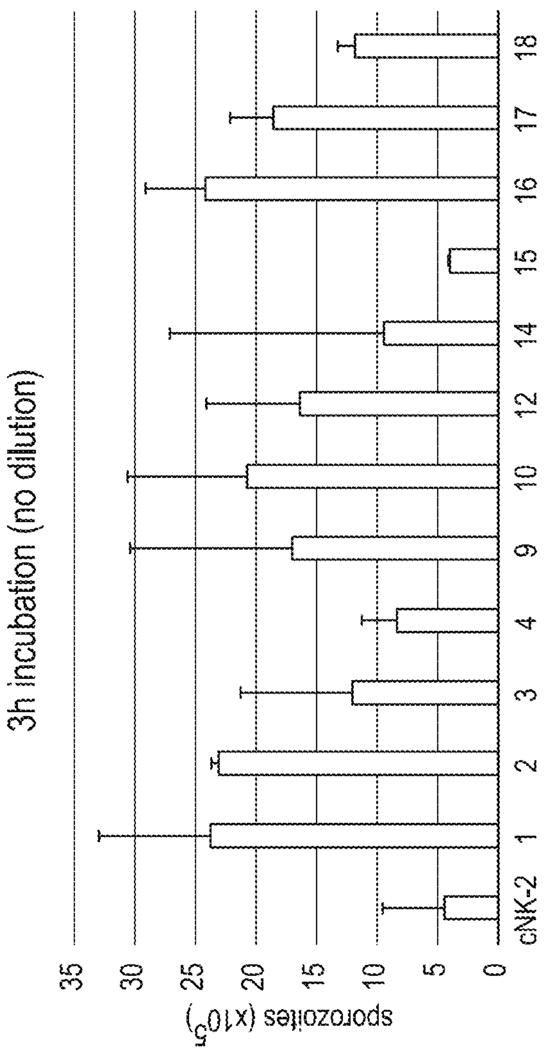
FIG. 6 *E. acervuline* sporozoite killing assay on culture supernatant from various isolated clones expressing secreted NK2 peptide. *E. acervulina* sporozoites were isolated from freshly prepared oocysts and mixed with supernatant in 1:1 ratio. After 3 h incubation at 41° C., the sporozoites were stained with fluorescence viability dye and counted. Clone #15 showed the highest killing activity.

Example 2. DATA presented in FIGS. 5 and 6 illustrate the utility of the secreted NK2 product in its efficacy to induce lysis upon microbial test samples. Now referring to FIG. 5, efficacy assay on culture supernatant from various isolated clones expressing secreted NK2 peptide. Total DNA was measured after 24 hr growth with or without the presence of cNK2 supernatant from *B. subtillis*. Kanamycin was used as a negative control and DH5alpha cells without any supernatant as a positive control. DH5alpha cells grown in the presence of *B. subtillis* supernatant without NK2 peptide showed no growth inhibition, whereas cells grown in the presence of *B. subtillis* supernatant with NK2 peptide showed growth inhibition comparable to Kanamycin. Clone #15 showed a high killing activity.

Now referring to FIG. 6, efficacy was further substantiated using an *E. acervuline* sporozoite killing assay on culture supernatant from various isolated clones expressing secreted NK2 peptide. *E. acervulina* sporozoites were isolated from freshly prepared oocysts and mixed with supernatant in 1:1 ratio. After 3 h incubation at 41° C., the sporozoites were stained with fluorescence viability dye and counted. Clone #15 showed the highest killing activity.

Example 3. Recombinant *B. subtilis* construction. Recombinant *B. subtilis* spores expressing empty vector (*B. subtilis*-EV) or chicken NK2 (*B. subtilis*-cNK2) was constructed and provided by US Biologic (Memphis, Tenn.). The NK-lysin used for the expression in a bacterial vector was based on the chicken NK-lysin sequence (RRQRSICKQLLKKLRQQLSDALQNNDD) (SEQ ID: No 6) which was then cloned into the pTTB2 expression vector (MoBiTec). Briefly, pTTB2-cNK was then expanded using BL21 competent *E. coli* (New England Biolabs, Inc., Ipswich, Mass.) and purified using the GeneJET Plasmid Miniprep Kit (Thermo Fischer Scientific, Madison, Wis.). Sequences were confirmed using Sanger sequencing and purified linearized plasmids were religated using Rapid DNA Ligation (Thermo Fisher Scientific, Madison, Wis.). Competent *Bacillus subtilis* cells (strain WB800N, MoBiTec) were transformed using 0.1 M EGTA and expanded on agar plates using 2% xylose as a selection agent. Single colonies were sequenced and expanded using 2xYT media (Difco).

In vitro killing assays *B. subtilis*-EV and *B. subtilis*-cNK2 were grown in media and culture supernatants were tested for anti-sporozoite activity using an in vitro assay as described (19). Briefly, sporocysts from freshly sporulated *E. acervulina* oocysts were harvested and purified using isopycnic centrifugation on a Percoll gradient followed by washing with ice-cold phosphate-buffered saline. Next, after sporocysts were treated with excystation solution (0.25% trypsin, 0.014 M taurocholic acid) and incubated for 30 min at 41° C. to release sporozoites. Afterward, sporozoites were harvested by filtering the excystation solution and washed three times with Hank's balanced salt solution (HBSS; Sigma-Aldrich, St. Louis, Mo., USA). *E. acervulina* sporozoites ($1.0\times10^7$/mL) were mixed with the culture supernatant from *B. subtilis*-EV and *B. subtilis*-cNK2 culture in 1:1 ratio.Chicken NK-lysin (Genscript, Piscataway, N.J.) was used as control at concentration of 100 µg/mL. After 3 h incubation at 41° C., the sporozoites were stained with fluorescence viability dye (AO/PI staining solution, Nexcelom BioscienceLLC, Lawrence, Mass.) and viable sporozoites were counted microscopically.

Chickens and Animal Care. Eighty-one-day-old Ross broiler chicks (Ross 708) were obtained from a local hatchery (Longnecker's Hatchery, Elizabethtown, Pa.) and housed in Petersime brooder units maintained in a temperature-controlled closed-house environment. Birds were raised to 14 days of age with non-medicated commercial starter diets. After 14 days, birds were moved to experimental grower cages and fed a non-medicated commercial grower diet until the end of the experimental period. *Ad libitum* feeds and fresh clean water were provided all the time.

On day 14, body weights were recorded, and chickens were randomly allocated to eight treatments (10 birds/2 cages/treatment; each bird considered as a replicate), whilst ensuring similar body weight distributions among treatments and replicates. Experimental treatments included: non-infected control (CON), infected control without any *B. subtilis* (NC), the infected treatment administered with *B. subtilis*-EVat three different dosages ($10^6$, $10^8$, and $10^{10}$ cfu/day/bird; EV6, EV8, and EV10, respectively), and the infected treatment with *B. subtilis*-cNK-2 at three different dosages ($10^6$, $10^8$, and $10^{10}$ cfu/day/bird; NK6, NK8, and NK10, respectively)(Table 1).

TABLE 1

Treatment and*Eimeria* challenge infections

| Treatment | Abbreviation | Description | *B. subtilis* dosage |
|---|---|---|---|
| Non-infected group | CON | — | — |
| Infected group | NC | *E. acervulina* | — |
| *B. subtilis* (Empty | EV6 | *E. acervulina*/ | $10^6$ cfu/mL |
| Vector) | EV8 | *B. subtilis* | $10^8$ cfu/mL |
| | EV10 | (EV) | $10^{10}$ cfu/mL |
| *B. subtilis* (cNK-2) | NK6 | *E. acervulina*/ | $10^6$ cfu/mL |
| | NK8 | *B. subtilis* | $10^8$ cfu/mL |
| | NK10 | (cNK-2) | $10^{10}$ cfu/mL |

Figure 8:
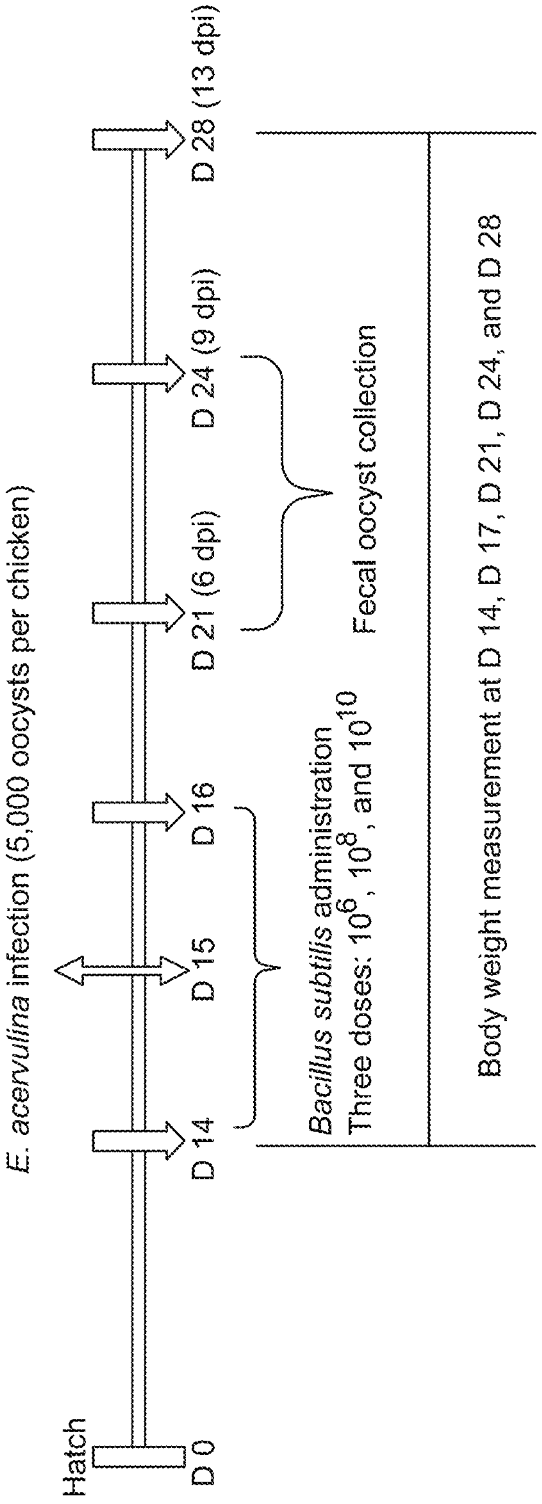
FIG. 8 Schematic outline of the experimental design

On day 14-16, groups receiving *B. subtilis* were administered their dedicated dose (1 mL/bird) using oral gavage (FIG. 8). Groups receiving *E. acervulina* challenge were challenged on day 15 with 5,000 freshly propagated *E. acervulinaoocysts* (ARS Beltsville strain #12)(20). Individual body weights were recorded for all chickens on day 14, 17, 21, 24, and 28. Pooled fecal samples were collected from each cage daily from day 21 (6 dpi) until day 24 (9 dpi). At the end of the experiment (28 days; 13 dpi), five birds from each treatment group were randomly selected for intestinal sample collection. Chickens were humanely sacrificed by cervical dislocation, and the spleen and 10 cm part of the mid-duodenum were dissected and stored in RNA stabilization solution (RNAlater™ solution, Invitrogen Corporation, Carlsbad, Calif.) at −20° C. The mucosa of the duodenum was scraped using a glass slide aseptically and stored in RNAlater at −20° C. until use.

Fecal oocyst assessment. The collected fecal samples were processed according to the method previously described (Lee et al., 2021). Briefly, feces collected from individual cages were ground and homogenized with 3 liters of water. Two subsamples from each cage were put into 50 mL tubes for oocyst counting. To count fecal oocysts, various dilutions were made initially to determine the optimum dilutions for enumeration of oocysts for each sample. Three different scientists independently counted oocysts microscopically using a McMaster counting chamber using a sodium chloride flotation method (21). The total number of oocysts shed per chicken was calculated using the following formula: Total oocysts/bird=(oocyst count×dilution factor× fecal sample volume/counting chamber volume)/number of birds per cage.

RNA extraction and qRT-PCR. Collected tissue samples were gently washed with ice-cold HBSS (Sigma-Aldrich, St. Louis, Mo., USA) and homogenized using a handheld homogenizer (TissueRuptor; Qiagen, Hilden, Germany). Total RNA was extracted using TRIzol reagent (Invitrogen) followed by DNase digestion as described (5). Quantification and purity were assessed using a NanoDrop spectrophotometer (NanoDrop One; Thermo Scientific) at 260/280 nm. Synthesis of cDNA was performed using a QuantiTect® Reverse Transcription Kit (Qiagen) according to the manufacturer's instructions. The gene expression levels of tight junction proteins such as JAM2, occludin, and ZO1, and mucin (MUC2) expression in the duodenum samples and antioxidant markers including SOD1, HMOX1, and CAT, in both duodenum and spleen samples were investigated. All oligonucleotide primer sequences used in this experiment are shown in Table 2. Table 2. Quantitative real-time PCR oligonucleotide primer sequences.

cate using Applied Biosystems QuantStudio 3 Real-Time PCR Systems (Life Technologies, Carlsbad, Calif.). The following PCR conditions were followed: denaturation at 95° C. for 10 min followed by amplification at 60° C. for 1 min for 40 cycles. Glyceraldehyde 3-phosphate dehydrogenase (GAPDH) was used as the reference gene for gene expression. For relative quantification of the gene expression levels, the logarithmic-scaled threshold cycle (Ct) values were used in the $2^{-\Delta\Delta Ct}$ method before calculating the mean and standard error of the mean (SEM) for the references and individual targets.

Data were analyzed using Mixed Model (PROC MIXED) in SAS. The individual bird was considered the experimental unit for statistical analysis. The results are given as least-squares means and pooled SEM. P-values<0.05 were considered to be significant. When the p-value between treatments was less than 0.05, homogeneous subsets were evaluated by the PDIFF option in SAS. The dose-response of growth performances were determined using the Interactive Matrix Language (IML) procedure of SAS to generate coefficients for the evenly spaced orthogonal contrasts. These coefficients generated by the IML procedure were then used in the mixed procedure for contrasts.

Figure 9:
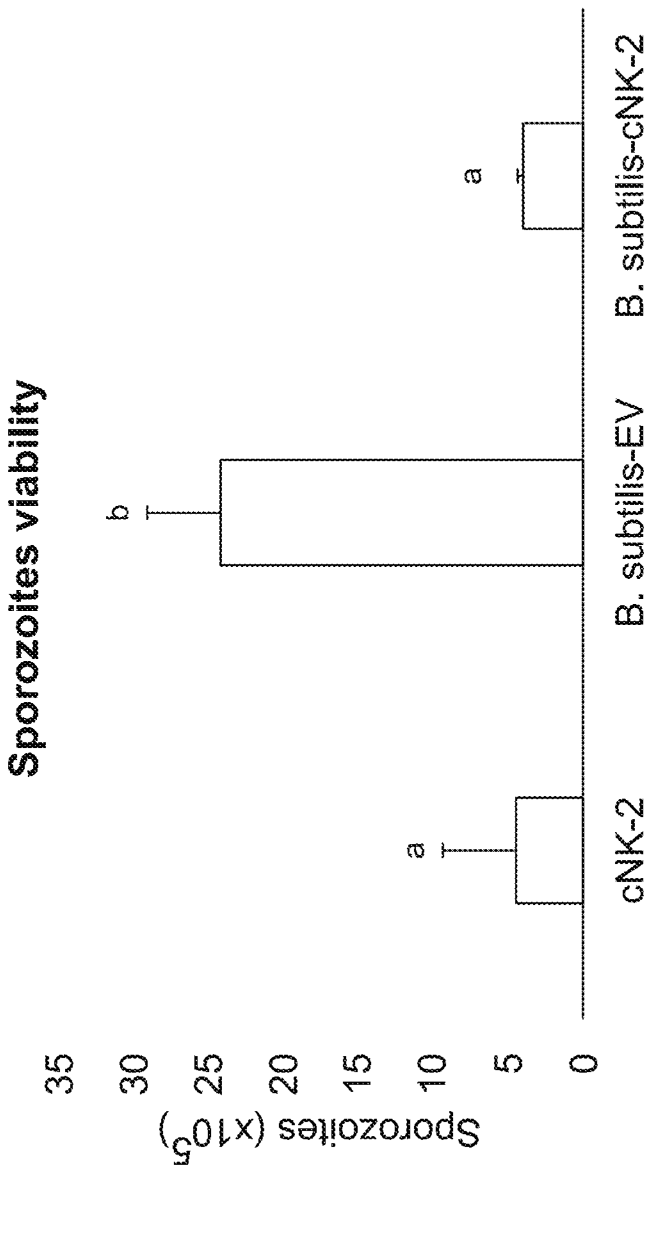
FIG. 9 shows Effect of *B. subtilis* expressing empty vector (*B. subtilis*-EV) or chicken c-NK2 (*B. subtilis*-cNK2) in vitro. *Eimeria acervulina* sporozoites ($1.0\times10^7$/mL) were incubated with culture supernatant from *B. subtilis*-EV and *B. subtilis*-cNK2. Chicken NK-lysin (cNK-2) was used as control at concentration of 100 μg/mL, for 3 h at 41° C. Sporozoites were stained with fluorescence viability dye and viable sporozoites were counted microscopically.$^{a-b}$ Bars with no common letter differ significantly (P<0.05).

In vitro assay for sporozoite viability. Sporozoites treated with chicken NK-lysin as a control showed a significant decrease(p<0.05) in sporozoites viability at the end of 3 h incubation period (FIG. 9). Culture supernatant from *B. subtilis*-cNK2 also showed a significant (p>0.05) sporozoites killing activity compared to control. However, sporozoites treated with the culture supernatant from *B. subtilis*-EV showed higher viability (p<0.05) compared to control and significantly higher (p<0.05) than the group treated with *B. subtilis*-cNK2 culture.

Body weights of all chickens did not significantly differ (d14: p>0.05) between groups at start of trial (table 3, FIG. 14).

There were no significant changes (p>0.05) between treatments at d 17 (2 dpi), regardless of *E. acervulina* infection or the type and dose of *Bacillus subtilis* administration. Chickens infected with *E. acervulina* showed lower

| Target gene | Primer sequence | Seq. Id. | Accession No. |
|---|---|---|---|
| GAPDH | F 5'-GGTGGTGCTAAGCGTGTTAT-3' | 7 | K01458 |
| | R 5'-ACCTCTGTCATCTCTCCACA-3' | 8 | |
| JAM-2 | F: 5'-AGCCTCAAATGGGATTGGATT | 9 | NM0,010,06257.1 |
| | R: 5'-CATCAACTTGCATTCGCTTCA | 10 | |
| OCLN | F: 5'-GAGCCCAGACTACCAAAGCAA | 11 | NM205,128.1 |
| | R: 5'-GCTTGATGTGGAAGAGCTTGTTG | 12 | |
| ZO-1 | F: 5'-CCGCAGTCGTTCACGATCT | 13 | XM01,527,8981.1 |
| | R: 5'-GGAGAATGTCTGGAATGGTCTGA | 14 | |
| MUC-2 | F: 5'-GCCTGCCCAGGAAATCAAG | 15 | NM0,013,18434.1 |
| | R: 5'-CGACAAGTTTGCTGGCACAT | 16 | |
| HMOX-1 | F 5'-CTGGAGAAGGGTTGGCTTTCT-3' | 17 | NM205344 |
| | R 5'-GAAGCTCTGCCTTTGGCTGTA-3' | 18 | |
| SOD1 | F 5'-ATTACCGGCTTGTCTGATGG-3' | 19 | NM205064.1 |
| | R 5'-CCTCCCTTTGCAGTCACATT-3' | 20 | |
| CAT | F 5'-ACTGCAAGGCGAAAGTGTTT-3' | 21 | NM001031215.1 |
| | R 5'-GGCTATGGATGAAGGATGGA-3' | 22 | |

Abbreviations: GAPDH, Glyceraldehyde 3-phosphate dehydrogenase; JAM-2, Junctional Adhesion Molecule 2; OCLN, Occludin; ZO-1, Zonula occludens-1; MUC-2, Mucin 2; HMOX-1, heme oxygenase 1; SOD1, Superoxide Dismutase 1; CAT, Catalase; F, forward primer; R, reverse The cDNA samples were diluted to 1:5, and 5-μL aliquots were used for qRT-PCR amplification. The sample was analyzed using SYBR Green qPCR Master Mix (PowerTrack, Applied Biosystems, Vilnius, Lithuania) in tripli- (p<0.05) body weight at d21 (6 dpi) than the CON chickens. However, the body weights of chickens in the NK10 group were significantly higher (p<0.05) than those of NC chickens at d24 (9 dpi). Chickens that received EV did not show (p>0.05) any dose responses for body weight measurement throughout the study period. In contrast, chickens in the NK groups showed enhanced body weights in a dose-dependent manner (p<0.05) at d21 and d24. Similar to the body weight data, no significant changes (p>0.05) were seen in the average daily gain (ADG) of chickens among the different treatment groups up to day 17 (2 dpi) (Table 3). Thereafter, chickens infected with *E. acervulina* showed significantly lower ($p<0.05$) ADG than the uninfected CON group. However, chickens in the NK10 group showed significantly increased ($p<0.05$) ADG compared to that of the NC group from d 17 to d24 (2 to 9 dpi). After d24, the NK10 group did not show any significant difference in ADG ($p>0.05$) compared to the control untreated chickens regardless of NK treatment dose.

Figure 10:
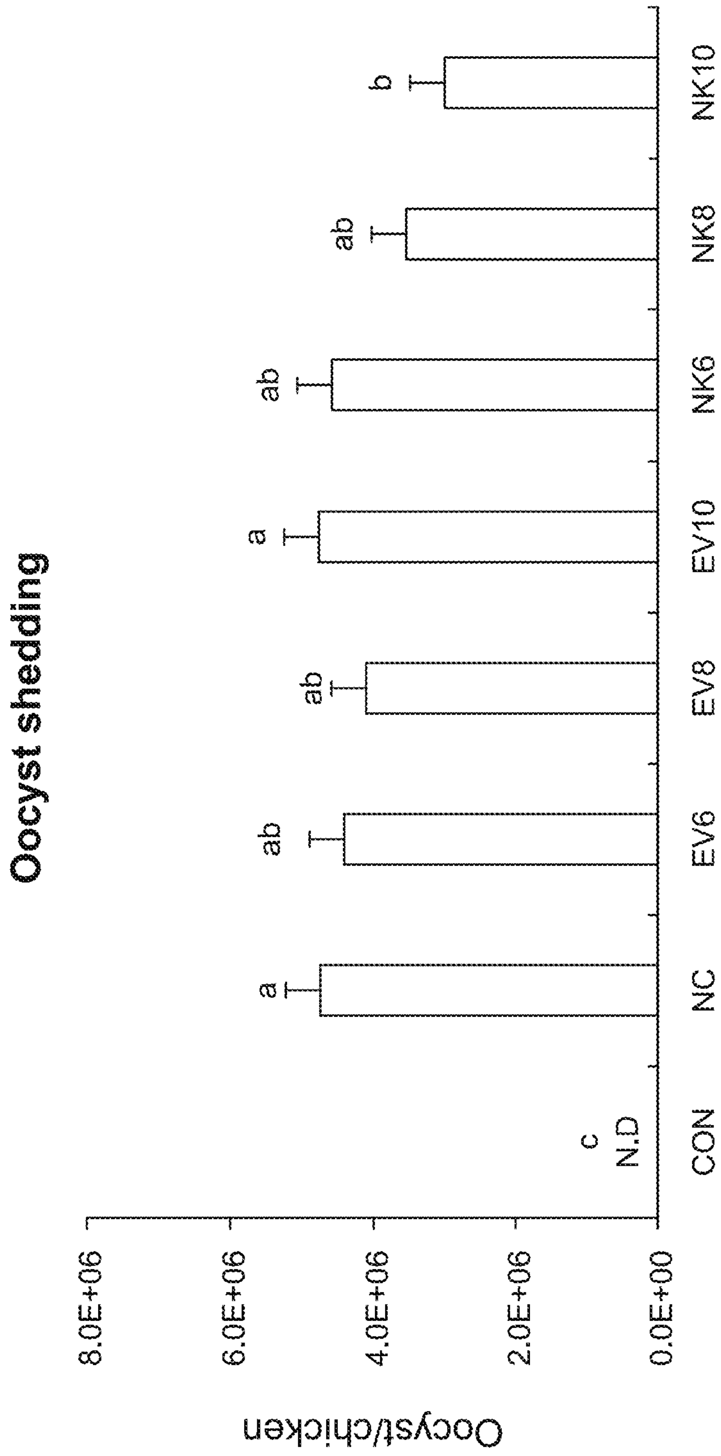
FIG. 10. shows fecal oocyst counts of *Eimeriaacervulina*-infected chickens fed daily oral treatment with *Bacillus subtilis*-cNK-2. All chickens except CON were infected by oral gavage at day 15 with 5,000 oocysts/chicken of *E. acervulina. Bacillus subtilis* were administrated by oral gavage at day 14 to 16. EV=*Bacillus* subtilis with empty vector, NK=*Bacillus subtilis* with cNK-2 NC=Non-*Bacillus subtilis,* EV6=*Bacillus subtilis* (empty vector) at $10^6$ cfu/day, EV8=*Bacillus subtilis*-EV at $10^8$ cfu/day, EV10=*Bacillus subtilis*-EV at $10^6$ cfu/day, NK6=*Bacillus subtilis*-cNK-2 at $10^6$ cfu/day, NK8=*Bacillus subtilis*-cNK-2 at $10^8$ cfu/day, NK10=*Bacillus subtilis*-cNK-2 at $10^{10}$ cfu/day, a~e Bars with no common letter differ significantly (P<0.05). Each bar represents the mean ±SEM (n=8). Fecal sample was collected from 6 to 9 dpi to calculate the oocyst shedding.
Figure 11A:
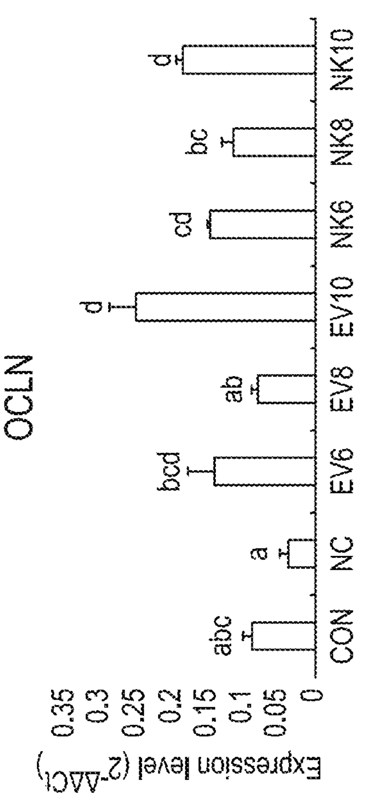
FIG. 11 shows tight junction gene expression in duodenal mucosa of *Eimeria acervulina*-infected broiler chickens fed orally *Bacillus subtilis* expressing cNK-2 (13 dpi). All chickens except CON were infected by oral gavage at day 15 with 5,000 oocysts/chicken of *E. acervulina. Bacillus subtilis* were administrated by oral gavage at day 14 to 16. EV=*Bacillus subtilis* (empty vector), NK=*Bacillus subtilis*-cNK-2 NC=*E. acervulina* infected non-*Bacillus* control, EV6=*Bacillus subtilis*-EV at $10^6$ cfu/day, EV8=*Bacillus subtilis*-EV at $10^8$ cfu/day, EV10=*Bacillus subtilis*-EV at $10^{10}$ cfu/day, NK6=*Bacillus subtilis*-cNK-2 at $10^6$ cfu/day, NK8=*Bacillus subtilis*-cNK-2 at $10^8$ cfu/day, NK10=*Bacillus subtilis*-cNK-2 at $10^{10}$ cfu/day. Transcript levels of A) occludin (OCLN), B) zonula occludens-1 (ZO1), C) junctional adhesion molecule 2 (JAM2), and D) Mucin-2 (MUC-2) in duodenal mucosa were measured by quantitative RT-PCR and genes expression were analyzed using the $2^{-\Delta\Delta Ct}$ method. a~d Bars with no common letter differ significantly (P<0.05). Each bar represents the mean ±SEM (n=5).
Figure 11B:
Figure 11C:
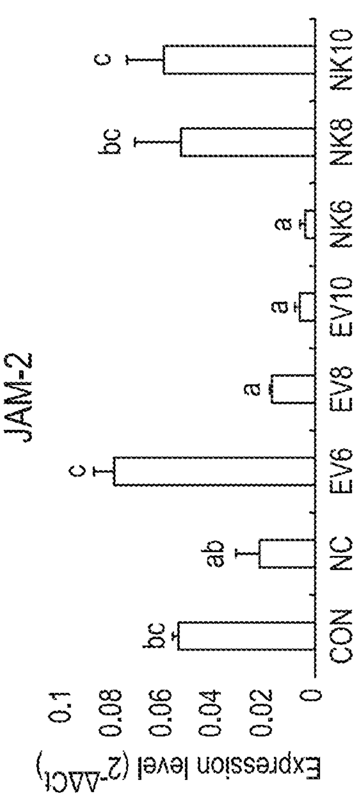
Figure 11D:
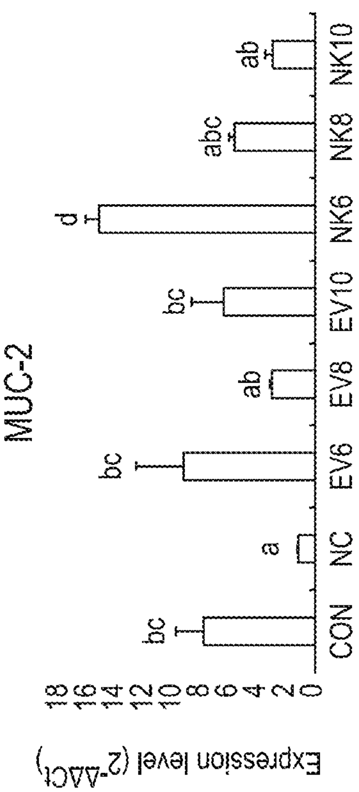

Fecal Oocyst shedding. Chickens that were treated with an oral dose of Bacillus subtilis carrying cNK2 showed significantly reduced ($p<0.05$) fecal oocyst output between 6 and 9 dpi (FIG. 10). In particular, the NK10 group showed significantly decreased oocyst shedding ($p<0.05$) compared to the NC group.

Gene expression of TJ proteins and mucin. Gene expression profiles of tight junction proteins in the duodenal mucosa are shown in FIG. 11. On 13 dpi, chickens in the NC group did not show any significant difference ($p>0.05$) in the expression levels of OCLN, ZO-1, and JAM-2 compared to the CON group. However, chickens that were given *B. subtilis* NK-lysin (NK6, NK8, and NK10) showed increased ($p<0.05$) OCLN gene expression compared to the NC chickens, regardless of doses of NK-lysin treatment. In comparison to *Bacillus subtilis* carrying cNK2 and *Bacillus subtilis* with empty vector, no difference ($p>0.05$) was observed in OCLN gene expression for each dose. Moreover, chickens in the NK8 and NK10 groups showed higher ($p<0.05$) expression of ZO-1 than chickens in the NC, EV8 and EV10 groups. Similarly, JAM-2 expression in the duodenum was higher ($p<0.05$) in the NK8 and NK10 treatment groups than in the EV8 and EV10 groups. Notably, MUC2 gene expression was lower ($p<0.05$) in NC chickens than in CON chickens but increased in the EV6, EV10, and NK6 groups compared to NC chickens.

Figure 12A:
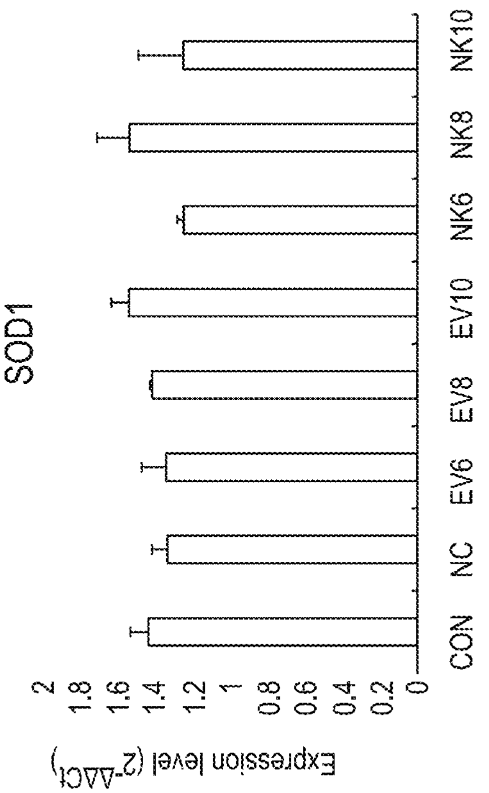
FIG. 12 shows antioxidant gene expression in duodenal mucosa of *Eimeria acervulina*-infected broiler chickens fed orally *Bacillus subtilis* expressing cNK-2 (13 dpi). All chickens except CON were infected by oral gavage at day 15 with 5,000 oocysts/chicken of *E. acervulina. Bacillus subtilis* were administrated by oral gavage at day 14 to 16. EV=*Bacillus subtilis* (empty vector), NK=*Bacillus subtilis*-cNK-2 NC=*E. acervulina* infected non-*Bacillus* control, EV6=*Bacillus subtilis* (empty vector) at $10^6$ cfu/day, EV8=*Bacillus subtilis* (empty vector) at $10^8$ cfu/day, EV10=*Bacillus subtilis* (empty vector) at $10^{10}$ cfu/day, NK6=*Bacillus subtilis*-cNK-2 at $10^6$ cfu/day, NK8=*Bacillus subtili*-scNK-2 at $10^8$ cfu/day, NK10=*Bacillus subtilis*-cNK-2 at $10^{10}$ cfu/day. Transcript levels of A) superoxide dismutase 1 (SOD1), B) catalase (CAT), C) heme oxygenase (HMOX1) in duodenal mucosa were measured by quantitative RT-PCR and genes expression were analyzed using the $2^{-\Delta\Delta Ct}$ method. a~d Bars with no common letter differ significantly (P<0.05). Each bar represents the mean ±SEM (n=5).
Figure 12B:
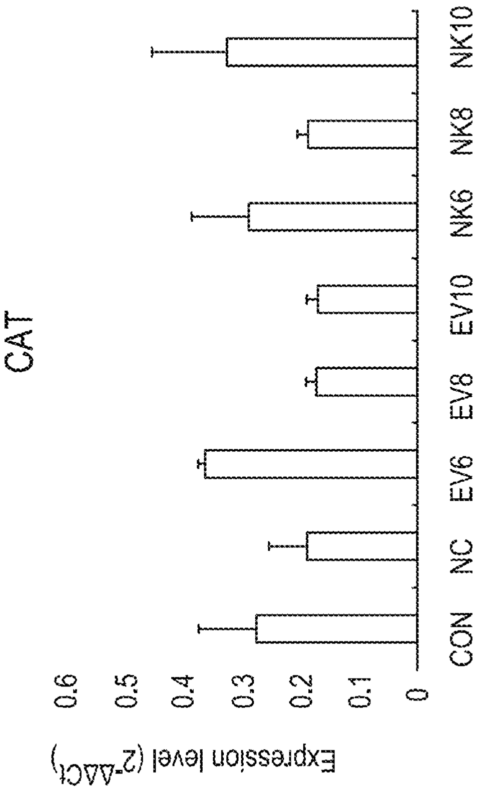
Figure 12C:
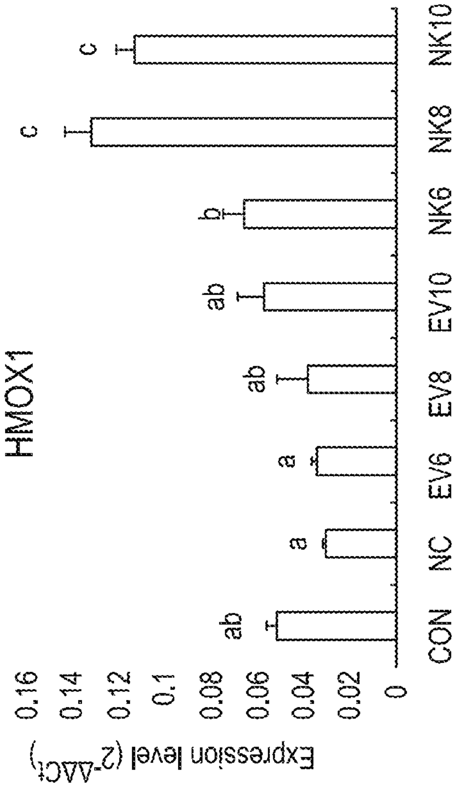

Antioxidant gene expression in the duodenal mucosa. FIG. 12 shows the mucosal antioxidant gene expression profile in the duodenum. Chickens treated with *B. subtilis* cNK-2 (NK6, NK8, and NK10) and infected with *E. acervulina* showed elevated ($p<0.05$) expression of HMOX1 in the duodenal mucosa (FIG. 12C) compared to the chickens in the *E. acervulina*-infected control (NC) group. There was no significant difference ($p>0.05$) in the expression levels of the SOD1 and CAT genes in the duodenal mucosa at 13 dpi (FIG. 12A-12B).

Figure 13B:
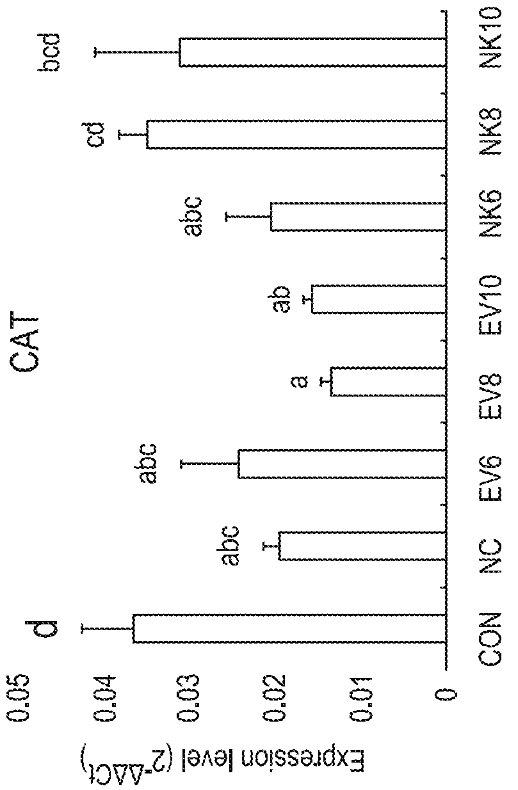
FIG. 13 shows antioxidant gene expression in spleen of *Eimeria acervulina*-infected broiler chickens fed orally *Bacillus subtilis* expressing cNK-2 (13 dpi). All chickens except CON were infected by oral gavage at day 15 with 5,000 oocysts/chicken of *E. acervulina. Bacillus subtilis* were administrated by oral gavage at day 14 to 16. EV=*Bacillus subtilis* (empty vector), NK=*Bacillus subtilis*-cNK-2 NC=*E. acervulina* infected non-*Bacillus* control, EV6=*Bacillus subtili*-EV at $10^6$ cfu/day, EV8=*Bacillus subtilis*-EV at $10^8$ cfu/day, EV10=*Bacillus subtilis*-EV at $10^{10}$ cfu/day, NK6=*Bacillus subtilis*-cNK-2 at $10^6$ cfu/day, NK8=*Bacillus subtilis*-cNK-2 at $10^8$ cfu/day, NK10=*Bacillus subtilis* cNK-2 at $10^{10}$ cfu/day. Transcript levels of A) superoxide dismutase 1 (SOD1), B) catalase (CAT), C) heme oxygenase (HMOX1) in spleen were measured by quantitative RT-PCR and genes expression were analyzed using the $2^{-\Delta\Delta Ct}$ method. a~d Bars with no common letter differ significantly (P<0.05). Each bar represents the mean ±SEM (n=5).
Figure 13A:
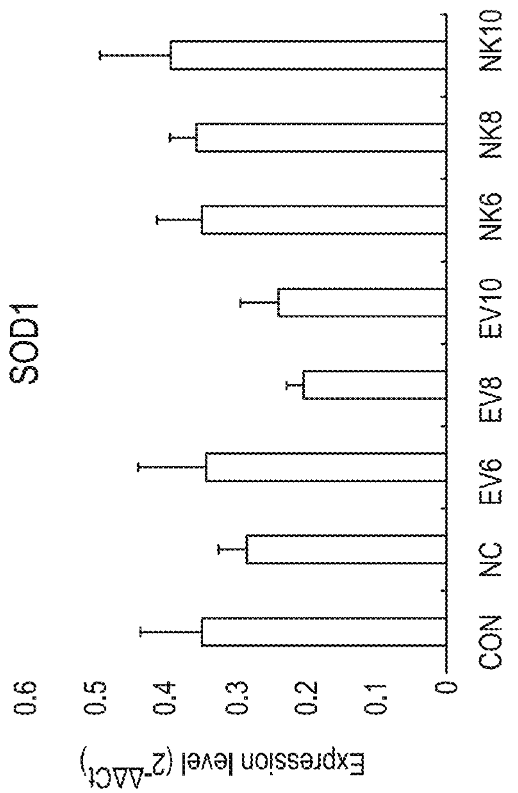
Figure 13C:
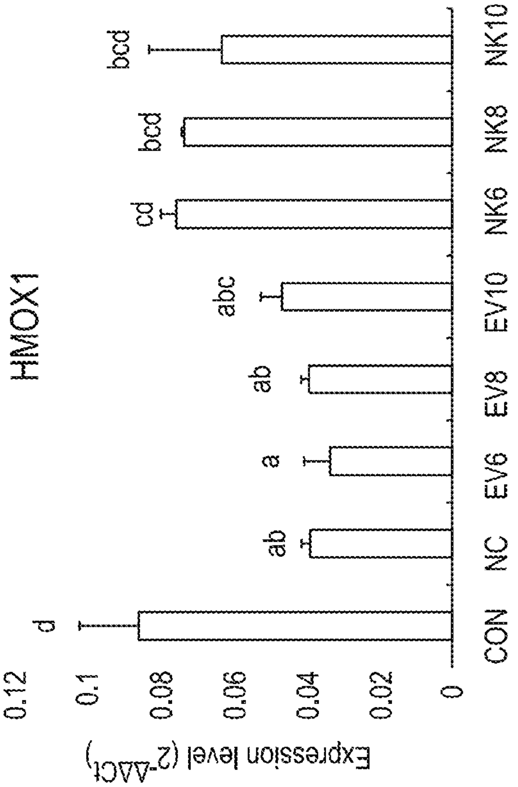

Antioxidant gene expression in spleen. Gene expression profiles of antioxidant genes in the spleen are shown in FIG. 13. The expression of CAT and HMOX1 was higher ($p<0.05$) in the CON group than in the NC and EV groups. Notably, chickens orally treated with higher doses of *B. subtilis* carrying cNK-2 (NK8 and NK10) showed similar ($p>0.05$) levels of expression as those of the CON group.

Example 4. In vivo Trials—Restoration of gut microbiome composition in *Eimeria* challenged chickens a total of 96 chickens were divided over four groups (24 chickens per group). Group 1 was non-treated, non-challenged, Group 2 was challenged with 5×10^3 *E. acervulina* and not treated, Group 3 was challenged with 5×10^3 *E. acervulina* and treated with *B. subtilis* vector only, and Group 4 was challenged with 5×10^3 *E. acervulina* and treated with *B. subtilis* expressing cNK-2 peptide. The therapeutically effective dose ranges from 1×10^6–1×10^12.

Chickens were treated on days 14 through 18 and challenged on day 15. At day 20, five chickens per group were sacrificed and duodenum and jejunum were collected. DNA was isolated from duodenum and jejunum samples and subjected to microbiome sequencing. Microbiome results were analyzed and visualized using R (R Core Team (2020). R: A language and environment for statistical computing. R Foundation for Statistical Computing, Vienna, Austria with dplyr (Hadley Wickham, Romain François, Lionel Henry and Kirill Müller (2021). dplyr: A Grammar of Data Manipulation. R package version 1.0.5. ggplot2 (H. Wickham. ggplot2: Elegant Graphics for Data Analysis. Springer-Verlag New York, 2016.), Hmisc (Frank E Harrell Jr, with contributions from Charles Dupont and many others. (2020). Hmisc: Harrell Miscellaneous. R package version 4.4-1. devtools (Hadley Wickham, Jim Hester and Winston Chang (2020). devtools: Tools to Make Developing R Packages Easier. R package version 2.3.2. vegan (Jari Oksanen, F. Guillaume Blanchet, Michael Friendly, Roeland Kindt, Pierre Legendre, Dan McGlinn, Peter R. Minchin, R. B. O'Hara, Gavin L. Simpson, Peter Solymos, M. Henry H. Stevens, Eduard Szoecs and Helene Wagner (2020). vegan: Community Ecology Package. R package version 2.5-7. https://CRAN.R-project.org/package=vegan and ggbiplot (Vincent Q. Vu (2011).), and ggbiplot: A ggplot2 based biplot. R package version 0.55.

Figure 15:
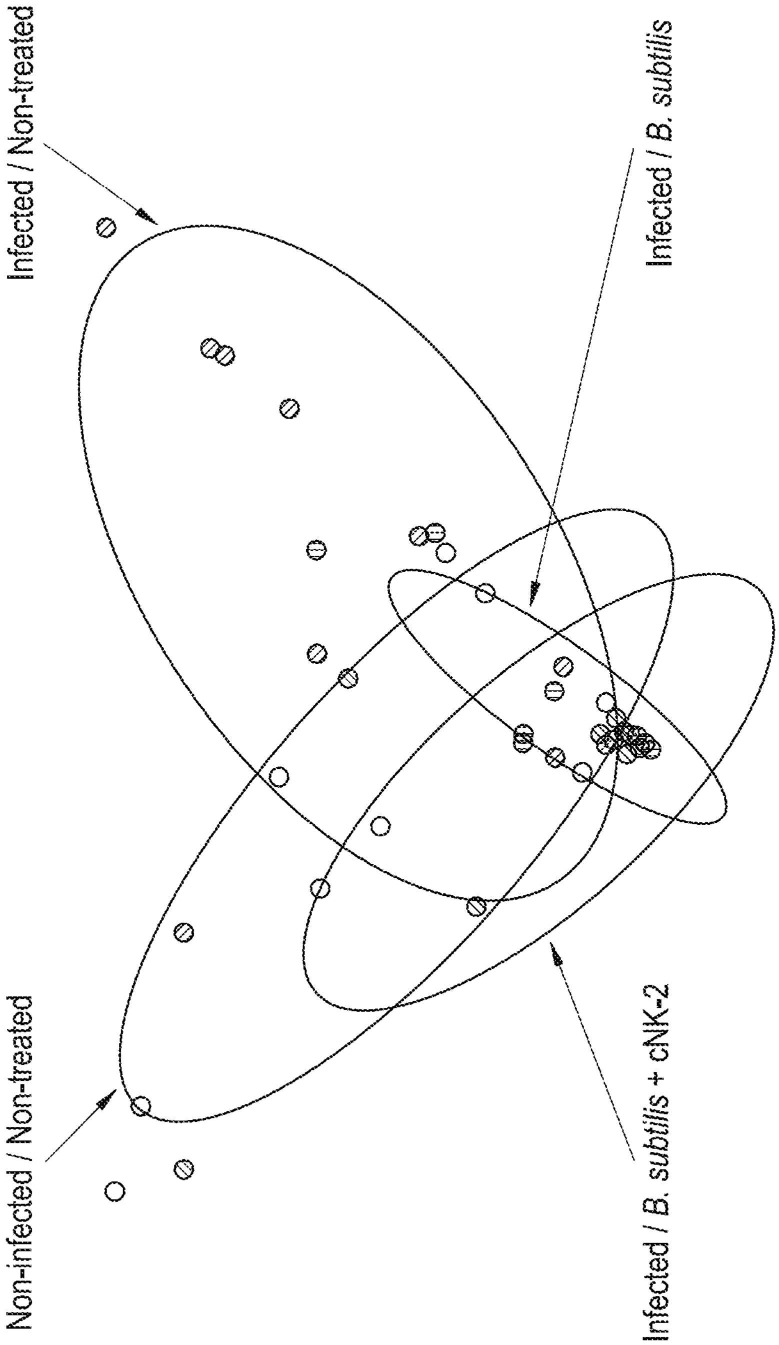
FIG. 15 shows that a probiotic expressing cNK-2 protects the chicken gut from microbiome alterations induced by an enteric parasite, which could not be achieved using probiotic treatment alone

Now referring to FIG. 15, cNK-2 showed preservation of the gut microbiome in *Eimeria* challenged chickens, as shown through principal component analysis on microbiome sequencing data from chicken gut tissues (samples represented by dots). Upper left oval: Microbiome composition in healthy control chickens (no treatment, no challenge). Upper right oval: Microbiome composition in chickens challenged with *Eimeria,* showing a significant shift in microbial gut occupancy. Lower right oval: Microbiome composition in chickens challenged with *Eimeria,* and treated with probiotic not expressing cNK-2, showing a microbial gut occupancy similar to untreated chickens. Lower left oval: Microbiome composition in chickens challenged with *Eimeria,* and treated with probiotic expressing cNK-2, showing a microbial gut occupancy similar to healthy chickens.

While the invention has been described with reference to details of the illustrated embodiments, these details are not intended to limit the scope of the invention as defined in the appended claims. The embodiment of the invention in which exclusive property or privilege is claimed is defined as follows:

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment. While the terms used herein are believed to be well understood by one of ordinary skill in the art, definitions are set forth herein to facilitate explanation of the presently disclosed subject matter.

INCORPORATION BY REFERENCE

All publications, patents and patent applications mentioned in this specification are herein incorporated by reference to the same extent as if each individual publication, patent or patent application was specifically and individually indicated to be incorporated by reference, Jacobs T. et al. (2003). NK-Lysin and Its Shortened Analog NK-2 Exhibit Potent Activities against *Trypanosome cruzi*. Antimicrobial Agents and Chemotherapy. 47, 607-613

Klein C. et al. (1992). Analysis of genes involved in biosynthesis of the antibiotic subtilin; Appl. and Environ. Microbiol. 58, 132-142

Lee S.H. et al. (2013). Parasiticidal activity of a novel synthetic peptide from the core α-helical region of NK-lysin. Vet. Parasitology.1 97, 113-121

Park et al. (2001). Bacillus subtilis MazF-bs (EndoA) is a UACAU-specific mRNA interferase; FEBS Lett. 585, 2526-2532

Pellegrini et al. (2005). The Bacillus subtilis ydcDE operon encodes an endoribonuclease of the MazF/Penk family and its inhibitor; Mol Microbiol. 56, 1139-1148

Simanshu D.K. et al. (2013). Structural basis of mRNA recognition and cleavage by toxin MazF and its regulation by antitoxin MazE in Bacillus subtilis; Mol Cell. 52, 447-458

Wickham, H. ggplot2: Elegant Graphics for Data Analysis. Springer-Verlag New York, 2016.

Yang S, et al.(2016). Construction of a novel, stable, food-grade expression system by engineering the endogenous toxin-antitoxin system in *Bacillus subtilis:* J of Biotech. 219, 40-47

What is claimed is:

1. A method to treat a subject in need of a treatment comprising:

orally administering a therapeutically effective amount of an antimicrobial peptide vectored composition comprising a bacterial protein expression vehicle comprised of a whole cell *Bacillus subtilis* transformed with a replicable plasmid DNA expression construct codon-optimized for expressing functionally active NK-2, wherein the subject is poultry and said poultry are in need of treatment for Avian coccidiosis, comprising the step of orally administering to the subject the therapeutically effective amount of the antimicrobial peptide vectored composition to induce cytotoxicity to treat an Avian coccidiosis infection.

2. The method of claim 1, wherein the subject is poultry and said poultry are in need of treatment to increase body weight, comprising the step of orally administering to the subject the therapeutically amount of a stable strain of a probiotic *B. subtilis* expressing cNK-2 to increase body weight of said subject.

* * * * *

UNITED STATES PATENT AND TRADEMARK OFFICE
CERTIFICATE OF CORRECTION

PATENT NO. : 11,814,628 B2
APPLICATION NO. : 18/008512
DATED : November 14, 2023
INVENTOR(S) : Jolieke Gerdy Van Oosterwijk et al.

It is certified that error appears in the above-identified patent and that said Letters Patent is hereby corrected as shown below:

On the Title Page

Item (72) Inventor Cyril Gray as shown should be corrected to read Cyril Gay

Signed and Sealed this
Tenth Day of September, 2024

Katherine Kelly Vidal
*Director of the United States Patent and Trademark Office*